US012730054B2

(12) United States Patent
Soper

(10) Patent No.: US 12,730,054 B2
(45) Date of Patent: Sep. 8, 2026

(54) NANO-COULTER COUNTER FOR DETECTION OF BIOLOGICAL NANOPARTICLES

(71) Applicant: University of Kansas, Lawrence, KS (US)

(72) Inventor: Steven Allan Soper, Baton Rouge, LA (US)

(73) Assignee: University of Kansas, Lawrence, KS (US)

( * ) Notice: Subject to any disclaimer, the term of this patent is extended or adjusted under 35 U.S.C. 154(b) by 149 days.

(21) Appl. No.: 18/844,006

(22) PCT Filed: Mar. 14, 2023

(86) PCT No.: PCT/US2023/064306
§ 371 (c)(1),
(2) Date: Sep. 4, 2024

(87) PCT Pub. No.: WO2023/178082
PCT Pub. Date: Sep. 21, 2023

(65) Prior Publication Data

US 2025/0189429 A1 Jun. 12, 2025

Related U.S. Application Data

(60) Provisional application No. 63/320,123, filed on Mar. 15, 2022.

(51) Int. Cl.
*G01N 15/12* (2024.01)
*G01N 15/00* (2024.01)
*G01N 33/543* (2006.01)

(52) U.S. Cl.
CPC ......... *G01N 15/131* (2024.01); *G01N 33/543* (2013.01); *G01N 2015/0038* (2013.01); *G01N 2015/135* (2024.01)

(58) Field of Classification Search
USPC ........................................................ 324/71.4
See application file for complete search history.

(56) References Cited

U.S. PATENT DOCUMENTS 2,656,508 A 10/1953 Coulter
2006/0246526 A1 11/2006 Inganas et al.
(Continued)

OTHER PUBLICATIONS

Shapiro, H. M., The evolution of cytometers. Cytometry. Part A : the journal of the International Society for Analytical Cytology 2004, 58 (1), 13-20.

(Continued)

*Primary Examiner* — Farhana A Hoque
(74) *Attorney, Agent, or Firm* — Pabst Patent Group LLP

(57) ABSTRACT

A nano-Coulter counter (nCC) device can include: an inlet; a plurality of nanochannels having a nanopore, wherein each nanochannel includes an inlet tapered region coupled to an inlet of the nanopore, wherein each nanopore has the second cross-dimension of at least about 50 nm to about 300 nm, and a pore length of at least about 50 nm to about 300 nm, wherein each nanochannel includes an outlet expansion region coupled to an outlet of the nanopore that expands from the second cross-dimension to a third cross-dimension that is larger than the second cross-dimension; an outlet microchannel fluidly coupled to an outlet of each of the plurality of nanochannels; an electrode pair having one electrode at the inlet microchannel and another electrode at the outlet microchannel; a power source electrically coupled with the electrode pair; and a pump operably coupled with the plurality of nanochannels.

15 Claims, 23 Drawing Sheets

(56) References Cited

U.S. PATENT DOCUMENTS

2012/0196376 A1 8/2012 Park et al.
2017/0253480 A1 9/2017 Turner et al.
2019/0234930 A1* 8/2019 Mayer .............. G01N 33/48721

OTHER PUBLICATIONS

Davey, H. M.; Kell, D. B., Flow cytometry and cell sorting of heterogeneous microbial populations: the importance of single-cell analyses. Microbiological Reviews 1996, 60 (4), 641-696.
Javanmard, M.; Davis, R. W., A microfluidic platform for electrical detection of DNA hybridization. Sensors and Actuators B: Chemical 2011, 154 (1), 22-27.
Javanmard, M.; Emaminejad, S.; Dutton, R. W.; Davis, R. W., Use of Negative Dielectrophoresis for Selective Elution of Protein-Bound Particles. Analytical Chemistry 2012, 84 (3), 1432-1438.
Emaminejad, S .; Javanmard, M .; Dutton, R. W .; Davis, R. W., Microfluidic diagnostic tool for the developing world: contactless impedance flow cytometry. Lab on a Chip 2012, 12 (21), 4499-4507.
Emaminejad, S.; Javanmard, M.; Dutton, R. W.; Davis, R. W., Smart Surface for Elution of Protein-Protein Bound Particles: Nanonewton Dielectrophoretic Forces Using Atomic Layer Deposited Oxides. Analytical Chemistry 2012, 84 (24), 10793-10801.
Song, Y.; Zhang, J.; Li, D., Microfluidic and Nanofluidic Resistive Pulse Sensing: A Review. Micromachines 2017, 8 (7), 204.
Traversi, F.; Raillon, C.; Benameur, S. M.; Liu, K.; Khlybov, S.; Tosun, M.; Krasnozhon, D.; Kis, A.; Radenovic, A., Detecting the translocation of DNA through a nanopore using graphene nanoribbons. Nature Nanotechnology 2013, 8 (12), 939-945.
Rodriguez-Trujillo, R.; Ajine, M. A.; Orzan, A.; Mar, M. D.; Larsen, F.; Clausen, C. H.; Svendsen, W. E., Label-free protein detection using a microfluidic Coulter-counter device. Sensors and Actuators B: Chemical 2014, 190, 922-927.
Cai, H.; Wang, Y.; Yu, Y.; Mirkin, M. V.; Bhakta, S.; Bishop, G. W.; Joshi, A. A.; Rusling, J. F., Resistive-Pulse Measurements with Nanopipettes: Detection of Vascular Endothelial Growth Factor C (VEGF-C) Using Antibody-Decorated Nanoparticles. Analytical Chemistry 2015, 87 (12), 6403-6410.
Han, Y.; Wu, H.; Liu, F.; Cheng, G.; Zhe, J., Label-Free Biomarker Assay in a Microresistive Pulse Sensor via Immunoaggregation. Analytical Chemistry 2014, 86 (19), 9717-9722.
Takakura, T.; Yanagi, I.; Goto, Y.; Ishige, Y.; Kohara, Y., Single-molecule detection of proteins with antigen-antibody interaction using resistive-pulse sensing of submicron latex particles. Applied Physics Letters 2016, 108 (12), 123701.
Pol, E. V. d.; Coumans, F. A. W.; Grootemaat, A. E.; Gardiner, C.; Sargent, I. L.; Harrison, P.; Sturk, A.; Leeuwen, T. G. v.; Niewuwland, R., Particle size distribution of exosomes and microvesicles determined by transmission electron microscopy, flow cytometry, nanoparticle tracking analysis, and resistive pulse sensing. Journal of Thrombosis and Haemostasis 2014, 12, 1182-1192.
Vogel, R.; Willmott, G.; Kozak, D.; Roberts, G. S.; Anderson, W.; Groenewegen, L.; Glossop, B.; Barnett, A.; Turner, A.; Trau, M., Quantitative Sizing of Nano/Microparticles with a Tunable Elastomeric Pore Sensor. Analytical Chemistry 2011, 83 (9), 3499-3506.
Roberts, G. S.; Yu, S.; Zeng, Q.; Chan, L. C. L.; Anderson, W.; Colby, A. H.; Grinstaff, M. W.; Reid, S.; Vogel, R., Tunable pores for measuring concentrations of synthetic and biological nanoparticle dispersions. Biosensors and Bioelectronics 2012, 31 (1), 17-25.
Fraikin, J.- L.; Teesalu, T.; McKenney, C. M.; Ruoslahti, E.; Cleland, A. N., A high-throughput label-free nanoparticle analyser. Nature Nanotechnology 2011, 6 (5), 308-313.
Xu, Y., Nanofluidics: A New Arena for Materials Science. Advanced Materials 2018, 30, 1702419.
Wanunu, M.; Dadosh, T.; Ray, V.; Jin, J.; McReynolds, L.; Drndić, M., Rapid electronic detection of probe-specific microRNAs using thin nanopore sensors. Nature nanotechnology 2010, 5 (11), 807-814.
Haque, F.; Li, J.; Wu, H.-C.; Liang, X.-J.; Guo, P., Solid-state and biological nanopore for real-time sensing of single chemical and sequencing of DNA. Nano Today 2013, 8 (1), 56-74.
Ying, Y.-L.; Cao, C.; Long, Y.-T., Single molecule analysis by biological nanopore sensors. Analyst 2014, 139 (16), 3826- 3835.
Davenport, M. W.; Healy, K.; Pevarnik, M.; Teslich, N.; Cabrini, S.; Morrison, A.; Siwy, Z. S.; Létant, S. E., The Role of Pore Geometry in Single Particle Detection. Biophysical Journal 2013, 104 (2, Supplement 1), 521a.
Deblois, R. W.; Wesley, R. K., Sizes and concentrations of several type C oncornaviruses and bacteriophage T2 by the resistive-pulse technique. Journal of virology 1977, 23 (2), 227-33.
Uram, J. D.; Ke, K.; Hunt, A. J.; Mayer, M., Submicrometer Pore-Based Characterization and Quantification of Antibody—Virus Interactions. Small 2006, 2 (8-9), 967-972.
Zhou, K.; Li, L.; Tan, Z.; Zlotnick, A.; Jacobson, S. C., Characterization of Hepatitis B Virus Capsids by Resistive-Pulse Sensing. Journal of the American Chemical Society 2011, 133 (6), 1618-1621.
Arjmandi, N.; Van Roy, W.; Lagae, L., Measuring Mass of Nanoparticles and Viruses in Liquids with Nanometer-Scale Pores. Analytical Chemistry 2014, 86 (10), 4637-4641.
Arjmandi, N.; Van Roy, W.; Lagae, L.; Borghs, G., Measuring the Electric Charge and Zeta Potential of Nanometer-Sized Objects Using Pyramidal-Shaped Nanopores. Analytical Chemistry 2012, 84 (20), 8490-8496.
Mcmullen, A.; de Haan, H. W.; Tang, J. X.; Stein, D., Stiff filamentous virus translocations through solid-state nanopores. Nature Communications 2014, 5 (1), 4171.
Wu, H.; Chen, Y.; Zhou, Q.; Wang, R.; Xia, B.; Ma, D.; Luo, K.; Liu, Q., Translocation of Rigid Rod-Shaped Virus through Various Solid-State Nanopores. Analytical Chemistry 2016, 88 (4), 2502-2510.
Karawdeniya, B. I.; Bandara, Y. M. N. D. Y.; Khan, A. I.; Chen, W. T.; Vu, H.-A.; Morshed, A.; Suh, J.; Dutta, P.; Kim, M. J., Adeno-Associated Virus Characterization for Cargo Discrimination through Nanopore Responsiveness. Nanoscale 2020, 12, 23721-23731.
Vogel, R.; Anderson, W.; Eldridge, J.; Glossop, B.; Willmott, G., A Variable Pressure Method for Characterizing Nanoparticle Surface Charge Using Pore Sensors. Analytical Chemistry 2012, 84 (7), 3125-3131.
Farkas, K.; Pang, L.; Lin, S.; Williamson, W.; Easingwood, R.; Fredericks, R.; Jaffer, M. A.; Varsani, A., A Gel Filtration-Based Method for the Purification of Infectious Rotavirus Particles for Environmental Research Applications. Food and Environmental Virology 2013, 5 (4), 231-235.
Akpinar, F.; Yin, J., Characterization of vesicular stomatitis virus populations by tunable resistive pulse sensing. Journal of Virological Methods 2015, 218, 71-76.
Saleh, O. A.; Sohn, L. L., An Artificial Nanopore for Molecular Sensing. Nano Letters 2003, 3 (1), 37-38.
Amarasekara, C. A.; Athapattu, U. S.; Rathnayaka, C.; Choi, J.; Park, S.; Soper, S. A., Open-tubular Nanoelectrochromatography (OT-NEC): Gel-free Separation of Single Stranded DNAs (ssDNAs) in Thermoplastic Nanochannels. Electrophoresis 2020, 41 (18-19).
Harms, Z. D.; Mogensen, K. B.; Nunes, P. S.; Zhou, K.; Hildenbrand, B. W.; Mitra, I.; Tan, Z.; Zlotnick, A.; Kutter, J. P.; Jacobson, S. C., Nanofluidic Devices with Two Pores in Series for Resistive-Pulse Sensing of Single Virus Capsids. Analytical Chemistry 2011, 83 (24), 9573-9578.
Zhe, J.; Jagtiani, A.; Dutta, P.; Hu, J.; Carletta, J., A micromachined high throughput Coulter counter for bioparticle detection and counting. Journal of Micromechanics and Microengineering 2007, 17, 304-313.
Becker, H., It's the Economy. Lab on a Chip 2009, 9, 2759-2762.
Nagura-Ikeda, M.; Imai, K.; Tabata, S.; Miyoshi, K.; Murahara, N.; Mizuno, T.; Horiuchi, M.; Kato, K.; Imoto, Y.; Iwata, M., Clinical evaluation of self-collected saliva by RT-qPCR, direct RT-qPCR, RT-LAMP, and a rapid antigen test to diagnose COVID-19. Journal of Clinical Microbiology 2020.
Zhao, Z.; Vaidyanathan, S.; Bhanja, P.; Gamage, S.; Saha, S.; Mckinney, C.; Choi, J.; Park, S.; Pahattuge, T.; Wijerathne, H.; Jackson, J. M.; Huppert, M. L.; Witek, M. A.; Soper, S. A., In-plane

(56) References Cited

OTHER PUBLICATIONS

Extended Nano-coulter Counter (XnCC) for the Label-free Electrical Detection of Biological Particles. Electroanalysis 2022, 34, 1-16.

Wijerathne, H.; Witek, M. A.; Jackson, J. M.; Brown, V.; Hupert, M. L.; Herrera, K.; Kramer, C.; Davidow, A. E.; Li, Y.; Baird, A. E.; Murphy, M. C.; Soper, S. A., Affinity enrichment of extracellular vesicles from plasma reveals mRNA changes associated with acute ischemic stroke. Nature Communications Biology 2021, 3, 613.

Pahattuge, T. N.; Jackson, M.; Digamber, R.; Wijerathne, H.; Brown, V.; Witek, M. A.; Perera, C.; Givens, R. S.; Peterson, B. R.; Soper, S. A., Visible photorelease of liquid biopsy markers following microfluidic affinity-enrichmentt. Chemical Communications 2020, 56, 4098-4101.

Uba, F. I.; Hu, B.; Weerakoon-Ratnayake, K.; Oliver-Calixte, N.; Soper, S. A., High process yield rates of thermoplastic nanofluidic devices using a hybrid thermal assembly technique. Lab on a Chip 2015, 15 (4), 1038-1049.

Pan, Y.; Zhang, D.; Yang, P.; Poon, L. L. M.; Wang, Q., Viral load of SARS-CoV-2 in clinical samples. The Lancet Infectious Diseases 2020, 20 (4), 411-412.

Weatherall, E.; Willmott, G. R., Conductive and Biphasic Pulses in Tunable Resistive Pulse Sensing. The Journal of Physical Chemistry B 2015, 119 (16), 5328-5335.

Menestrina, J.; Yang, C.; Schiel, M.; Vlassiouk, I.; Siwy, Z. S., Charged Particles Modulate Local Ionic Concentrations and Cause Formation of Positive Peaks in Resistive-Pulse-Based Detection. The Journal of Physical Chemistry C 2014, 118 (5), 2391-2398.

Song, Y.; Song, J.; Wei, X.; Huang, M.; Sun, M.; Zhu, L.; Lin, B.; Shen, H.; Zhu, Z.; Yang, C., Discovery of Aptamers Targeting Receptor-Binding Domain of the SARS-CoV-2 Spike Glycoprotein. 2020.

Chai, Z.; Guo, L.; Jin, H.; Li, Y.; Du, S.; Shi, Y.; Wang, C.; Shi, W.; He, J., Tba loop mapping with 3'-inverted-deoxythymidine for fine-tuning of the binding affinity for α-thrombin. Organic & Biomolecular Chemistry 2019, 17 (9), 2403-2412.

Ni, S. Y., H.; Wang, L.; Lu, J.; Jiang, F.; Lu, A.; Zhang, G. , Chemical Modifications of Nucleic Acid Aptamers for Therapeutic Purposes. Int. J. Mol. Sci. 2017, 18, 1683.

Pahattuge, T. N.; Jackson, J. M.; Digamber, R.; Wijerathne, H.; Brown, V.; Witek, M. A.; Perera, C.; Givens, R. S.; Peterson, B. R.; Soper, S. A., Visible photorelease of liquid biopsy markers following microfluidic affinity-enrichment. Chemical Communications 2020, 56 (29), 4098-4101.

Gamage, S. S. T.; Pahattuge, T.; Wijerathne, H.; Childers, K.; Vaidyanathan, S.; Athapattu, U. S.; Zhang, L.; Zhao, Z.; Hupert, M. L.; Muller, R. M.; Muller-Cohn, J.; Geisbrecht, B. V.; Pathak, H.; Pessetto, Z.; Gan, G.; Choi, J.; Park, S.; Godwin, A. K.; Witek, M. A.; Soper, S. A., Microfluidic Affinity Selection of Active SARS-CoV-2 Virus Particles Science Advances 2022, 8, (accepted for publication).

Shu, Y.; McCauley, J., GISAID: Global initiative on sharing all influenza data—from vision to reality. Euro Surveill 2017, 22 (13).

Scudellari, M., How the coronavirus infects cells—and why Delta is so dangerous. Nature 2021, 595 (7869), 640-644.

Kim, Y. G.; Yun, S. G.; Kim, M. Y.; Park, K.; Cho, C. H.; Yoon, S. Y.; Nam, M. H.; Lee, C. K.; Cho, Y. J.; Lim, C. S., Comparison between Saliva and Nasopharyngeal Swab Specimens for Detection of Respiratory Viruses by Multiplex Reverse Transcription-PCR. J Clin Microbiol 2017, 55 (1), 226-233.

R. W. DeBlois and C. P. Bean, "Counting and Sizing of Submicron Particles by the Resistive Pulse Technique", Review of Scientific Instruments, 1970, 41, 909-916.

E. C. Gregg and K. D. Steidley, "Electrical Counting and Sizing of Mammalian Cells in Suspension", Biophys J, 1965, 5, 393-405.

W. R. Smythe, "Flow Around a Spheroid in a Circular Tube", The Physics of Fluids, 1964, vol. 7, No. 5, 633-638.

United States Patent and Trademark Office; International Search Report and Written Opinion issued in PCT/US23/64306 dated Aug. 4, 2023; 12 pages.

* cited by examiner

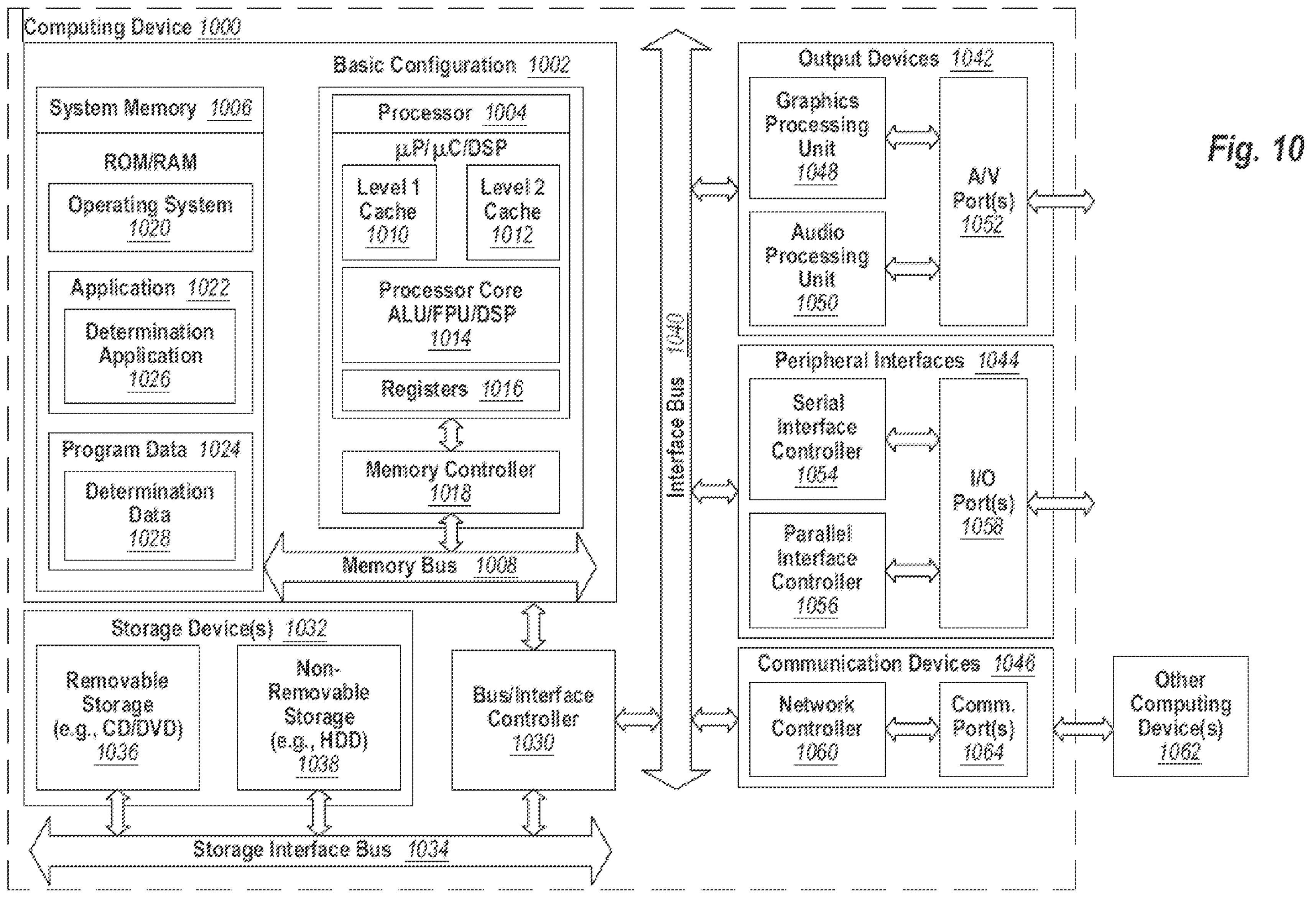
Fig. 10
Computing Device 1000
Basic Configuration 1002
System Memory 1006
ROM/RAM
Operating System 1020
Application 1022
Determination Application 1026
Program Data 1024
Determination Data 1028
Processor 1004
µP/µC/DSP
Level 1 Cache 1010
Level 2 Cache 1012
Processor Core ALU/FPU/DSP 1014
Registers 1016
Memory Controller 1018
Memory Bus 1008
Storage Device(s) 1032
Removable Storage (e.g., CD/DVD) 1036
Non-Removable Storage (e.g., HDD) 1038
Bus/Interface Controller 1030
Storage Interface Bus 1034
Interface Bus 1040
Output Devices 1042
Graphics Processing Unit 1048
Audio Processing Unit 1050
A/V Port(s) 1052
Peripheral Interfaces 1044
Serial Interface Controller 1054
Parallel Interface Controller 1056
I/O Port(s) 1058
Communication Devices 1046
Network Controller 1060
Comm. Port(s) 1064
Other Computing Device(s) 1062

NANO-COULTER COUNTER FOR DETECTION OF BIOLOGICAL NANOPARTICLES

CROSS-REFERENCE TO RELATED APPLICATIONS

This patent application claims priority to U.S. Provisional Application No. 63/320,123 filed Mar. 15, 2022, which provisional is incorporated herein by specific reference in its entirety.

U.S. GOVERNMENT RIGHTS

This invention was made with government support under HL152410 awarded by the National Institutes of Health. The government has certain rights in the invention.

BACKGROUND

Field

The present disclosure relates to affinity selection devices and nano-Coulter Counter devices for use in detecting biological nanoparticles.

Description of Related Art

Previously, particle counters have been known to be used for counting cells. Resistive pulse sensors (RPS) are operated by driving particles through a narrow constriction (i.e., pore) between two reservoirs of a conductive solution to cause transient perturbation of the pore's conductance.[1-4] The perturbation can be detected by a temporary change in the measured ionic current in the pore. The magnitude and duration of the measured perturbation can be used to determine the size and speed of the particle through the pore, and the number of perturbations per unit of time can be used to correlate with the concentration of particles in the sample.[5-8] The RPS can be configured to have a pore size that is commensurate with the target particle size to be detected. The RPS can also be referenced as a Coulter-counter.

The RPS can be used to detect single molecules, such as nucleic acids and proteins, as well as single particles.[9-13] Other platforms are also capable of detecting biological particles.[14-17] The challenge with RPS is that the pore size must be adjusted to accommodate the size of the particles being analyzed; the size range of particles that can be detected with respect to the pore size is ~5-fold.[14] In addition, due to the small size of the pore, the volume throughput and sampling efficiency can be quite low giving rise to modest concentration limits-of-detection (LOD).

The RPS typically uses biological or synthetic pores.[20-29] There are two main types of synthetic pores: (1) Out-of-plane pores in which the pore is configured perpendicular to the fluidic elements; and (2) in-plane pores in which the pore is parallel with respect to the associated fluidic network. Also, the RPS may be tunable that can adjust the size of the out-of-plane pores.[30-32] However, in-plane pores are advantageous over out-of-plane formats because the pores can be integrated into a fluid network facilitating the ease of fabrication using top-down strategies, unique measurement modalities not available using out-of-plane sensors, ability to integrate sample preparation to the RPS, and increased sample transfer of analytes to the sensing pores.[33-37]

Detection of viral particles can be important for diagnostics, but there are certain ranges of viral particles present in biological samples, such as from 500-$10^8$ viral particles/mL.[39] Therefore, it can be advantageous to be able to easily and accurately detect viral particles at the biological concentration ranges.

Previously, single pore detection devices have been used.[40] However, deficiencies in the poor concentration of LOD may be problematic when testing for viral particles or other biological nanoparticles, such as exosomes.

SUMMARY

In some embodiments, a nano-Coulter counter (nCC) device can include: an inlet microchannel; a plurality of nanochannels fluidly coupled to the inlet microchannel having a first cross-dimension, each nanochannel having a nanopore with a second cross-dimension that is narrower than the first cross-dimension, wherein each nanochannel includes an inlet tapered region coupled to an inlet of the nanopore that tapers from the first cross-dimension to the second cross-dimension, wherein each nanopore has the second cross-dimension of at least 50 nm to about 300 nm, and a pore length of at least 50 nm to about 300 nm, wherein each nanochannel includes an outlet expansion region coupled to an outlet of the nanopore that expands from the second cross-dimension to a third cross-dimension that is larger than the second cross-dimension; an outlet microchannel fluidly coupled to an outlet of each of the plurality of nanochannels; an electrode pair having a working electrode at the inlet microchannel and a ground electrode at the outlet microchannel; a power source electrically coupled with the electrode pair; and a pump operably coupled with the plurality of nanochannels. In some aspects, the nCC consisting of five of the nanochannels. In some aspects, the inlet tapered region includes an opening at the inlet microchannel. In some aspects, a pressure sensor is operably coupled with the outlet microchannel. In some aspects, the inlet microchannel, plurality of nanochannels, and outlet microchannel are formed of cyclic olefin polymer or other plastic.

In some embodiments, a detection system can include: a selection device comprising a microfluidic device having a plurality of pillars forming a plurality of flow paths, wherein an affinity-selection agent is coupled to the plurality of pillars by a stimulus-cleavable linker; and the nano-Coulter counter device of claim one of the embodiments. In some aspects, the affinity selection agent is selected from a monoclonal antibody or an aptamer. In some aspects, the detection system can include a controller configured for controlling operation of the selection device and nano-Coulter counter. In some aspects, the detection system includes a means for providing stimulus to the stimulus-cleavable linker. In some aspects, the means for providing the stimulus to the stimulus-cleavable linker is selected from the group consisting of: a chemical input means, wherein the chemical cleaves the linker; light input means, wherein light cleaves the linker; sound input means, where sound cleaves the linker; heat input means, wherein heat cleaves the linker; or combinations thereof.

In some embodiments, a method of detecting a particle can include: providing the nano-Coulter counter of one of the embodiments; introducing a composition including particles having a particle range of about 50 nm to about 175 nm into the inlet microchannel of the nano-Coulter counter; applying a current with the power source to cause current to flow from working electrode to the ground electrode; recording a current data trace for the current; detecting a perturbation in the current data trace that is above a threshold; and determining the composition to have the particle. In some aspects, the flow rate of the composition in the microchannel is from about 0.1 μL/min to 10 μL/min. In some aspects, the voltage of the power source is from about 1 V to about 5 V. In some aspects, the nano-Coulter counter has a limit of detection of at least about $2.4 \times 10^3$ particles/mL, or within 25% thereof.

In some embodiments, a method of detecting a particle can include: providing the detection system of one of the embodiments; introducing a sample suspected of having particles into the selection device; capturing the particles with the affinity-selection agent; releasing the particles from the pillars into a composition by cleavage of the stimulus-cleavable linker; introducing the composition including particles having a particle range of about 50 nm to about 175 nm into the inlet microchannel of the nano-Coulter counter; applying a current with the power source to cause current to flow from working electrode to the ground electrode; recording a current data trace for the current; detecting a perturbation in the current data trace that is above a threshold; and determining the composition to have the particle. In some aspects, the methods include controlling fluid flow in the nanochannels with the pump.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 1 illustrates an example embodiment of a system having a selection device and a nano-Coulter Counter (nCC).

FIG. 10 illustrates an embodiment of a computing device that can be used as a controller of the systems and that can be used for performing computing functions, analyzing data, determining operating protocols, and implementing the methods described herein.

Figure 2:
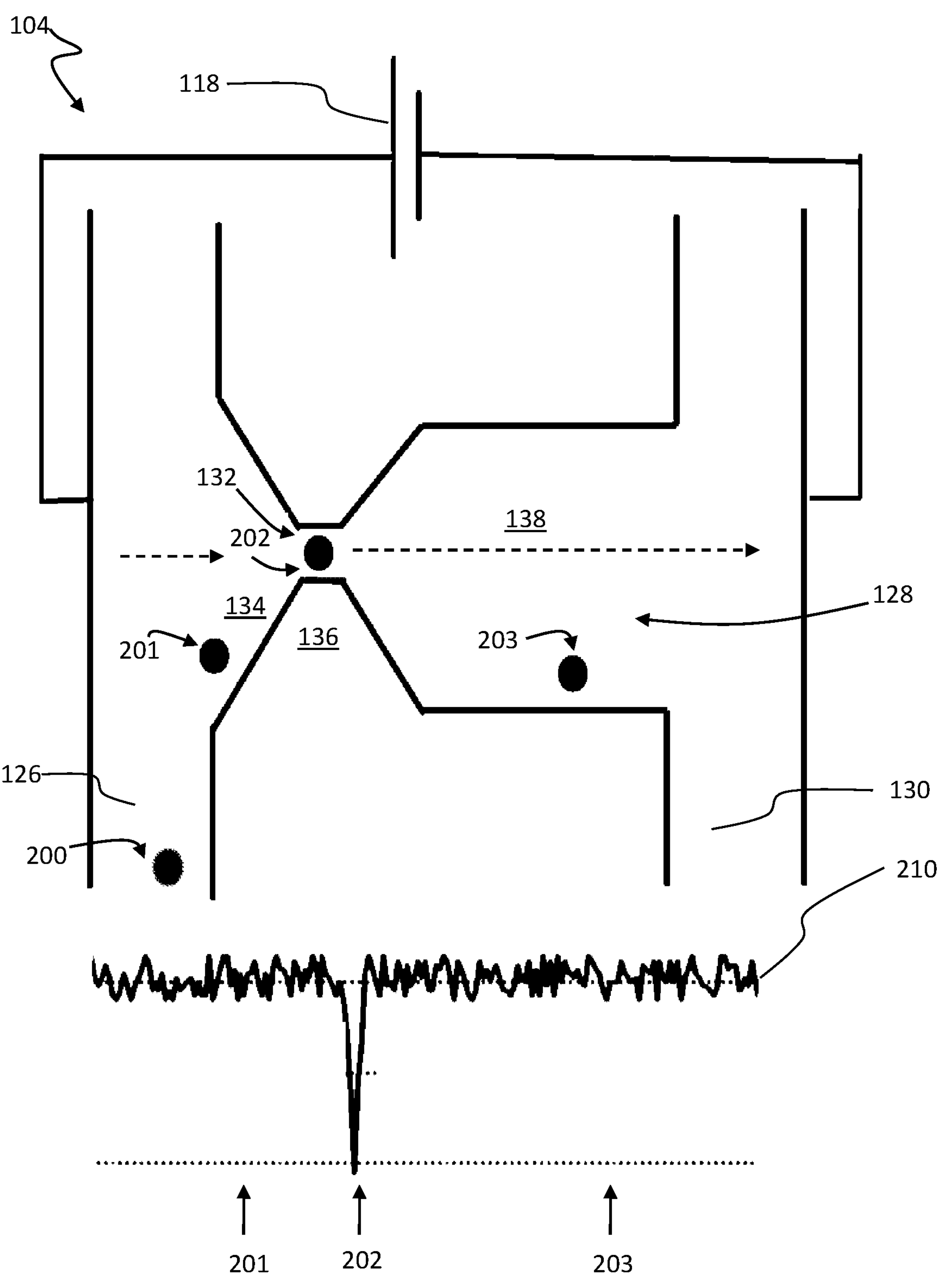
FIG. 2 illustrates an example of a pore of a nCC.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology relates to a detection system having an affinity-selection device configured to select a target particle from a sample and having a chip-based nano-Coulter counter (nCC) that can detect the nanoparticles that are affinity-selected from biological samples with a high concentration limit-of-detection. In some aspects, the new nCC surpasses existing resistive pulse sensors by 2-3 orders of magnitude in terms of their concentration limit-of-detection. The nCC can include a plurality (e.g., 3, 4, 5, 6, 7, etc.) of in-plane pores. Each in-plane pore can have an effective diameter of about 250-450 nm (e.g., 350 nm) placed in parallel. Each in-plane pore can be configured to provide high detection efficiency for single particles translocating both hydrodynamically and electrokinetically through these pores.

Figure 1:
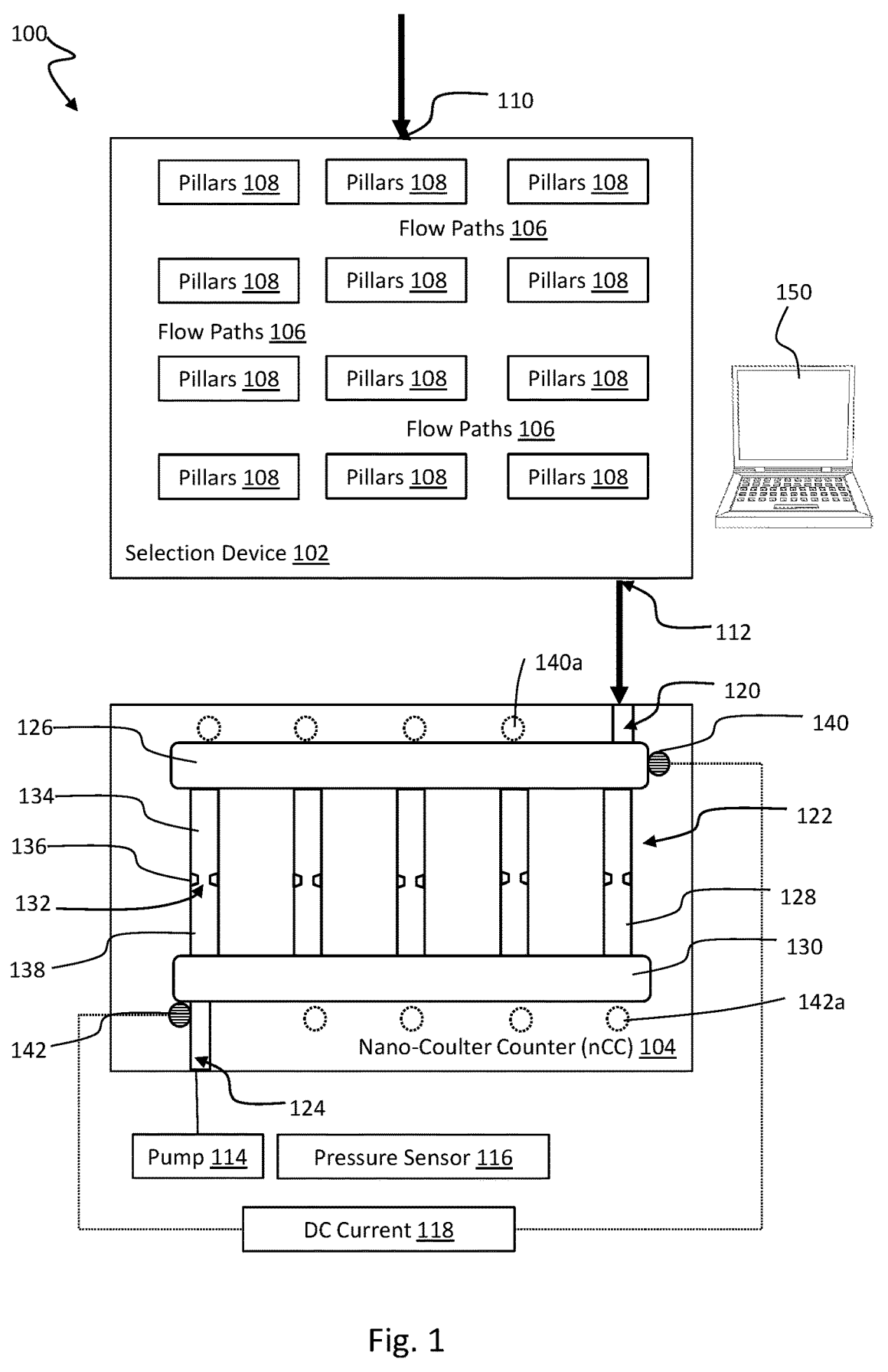

FIG. 1 shows an embodiment of the detection system 100 having the affinity-selection device 102 and the nCC device 104. The affinity-selection device 102 can include an inlet 110 that partitions into a plurality of flow paths 106 that are formed by a plurality of pillars 108 (e.g., pillared microfluidic chip[41]), which are located between the inlet 110 and an outlet 112. The pillars 108 are coated with an affinity-selection agent that binds with an affinity selection target on a particle. This allows for the affinity-selection agent to selectively bind with the target on the particle. The affinity-selection agent can be any structure or entity that has an affinity for selection of the target so as to selectively bind with the target over other non-targets. This allows selection of the particles with the target over particles that do not have the target. Examples of affinity-selection agents can include antibodies, antibody fragments, receptor-targeting ligands, aptamers, or the like. Accordingly, the affinity-selection agent can be selected based on the availability of targets on the particle to be detected. The affinity-selection agent can be linked to the pillars 108 via a cleavable bond (e.g., photocleavable linker[42], such as heterobifunctional, 7-aminocoumarin photocleavable (PC) linker with unique properties to covalently attach affinity-selection agent to surfaces and subsequently release them with visible light (400-450 nm)), which allows for selective cleaving of the bond to release the captured particles. These released particles are then provided to the nCC for detection and counting.

The nCC can include an inlet 120 and a fluidic network 122 to an outlet 124. The fluidic network 122 can have an inlet microchannel 126 connected through a plurality of nanochannels 128 (e.g., five (5) nanochannels 128 being preferred) to an outlet microchannel 130. The outlet microchannel 130 is connected to the outlet 124. The fluidic network 122 can include a pump 114 to facilitate and control fluidic flow and fluid flow rate within the nanochannels 128. The nanochannels 128 include constrictors 136 that constrict the diameter of the throat 132 to form the pore. Therefore, the mouth 134 of each nanochannel 128 is wider than the throat 132 of the pore. The nanochannel outlet 138 can be the same size (e.g., width and height) or different size from the respective mouth 134. The outlet microchannel 130 may be the same size or different from the inlet microchannel 126. Additionally, a pressure sensor 116 can be associated with the fluidic network 112 so as to be able to measure variations in pressure. A circuit is formed by having the working electrode 140 at the inlet 120 and a ground electrode 142 at the outlet 124, which are connected to a power source 118 that provides DC current. Optionally, a working electrode 140*a* can be across from the mouth 134 of each nanochannel 128 with a ground electrode 142*a* across from the nanochannel outlet 138, which can be connected to the power source 118, or a power source for each electrode pair.

Also, a computing system 150 configured as a controller and data processor can be included. The computing system can include a non-transient memory device having computer-executable instructions for operating the selection device 102 and nCC 104, obtaining data therefrom, analyzing the data, modulating operations, or providing operational reports. The computing system 150 can generate a report on the detected particles.

FIG. 2 shows an embodiment of a nCC device 104 with a nanopore 132 that is capable of being used as a RPS. The nCC 104 can be configured for detecting particles. Notably, only a portion of the microchannel 126 is shown and only one of the nanochannels 128 is shown to connect to the outlet microchannel 138. As such, the two access microchannels 126, 130 are connected by a nanopore 132 having the constrictor 136 that forms the throat of the nanopore 132 between the mouth 134 and nanochannel outlet 138. The nanochannel 128 is connected to an electrical circuit with the power source 118 as shown. When the particles 200 are in microchannel 126, there is a constant current produced expressed in the current data measurement trace 210. When the particle 201 moves into the mouth 134 of the nanochannel 128 of the nCC 104 it is directed towards the throat of the nanopore 132 and there is no change in the current data measurement trace 210. However, when the particle 202 moves into the throat of the nanopore 132, there is a drop in current that is generated due to the blockage of current produced by the particle 202, which is shown at the peak for particle 202. The current resumes to the baseline when the particle 202 moves from the throat of the nanopore 132 of the nCC 104 into the nanochannel outlet 138 and into the outlet microchannel 130.

In some embodiments, the experimental setup with the nCC device 104 is performed in three stages: Stage 1, where microchannel 126 is filled with the sample and the outlet microchannel 130 is filled with the buffer. A ferrule can be used to connect a syringe pump (114) that withdraws at about 20 μl/min on the buffer side or outlet microchannel 130, while the other end of the buffer is sealed. The setup is connected to an electrical circuit with a power source 118 to measure the current.

The nanochannel can have various dimensions, which can vary. The length of the nanochannel can be from 5 microns to 25 microns, from 10 microns to 20 microns, or about 15 microns. The height/depth of the nanochannel can have a dimension of about 300 microns to about 1000 nm, or about 400 nm to about 800 nm, or about 500 nm to about 600 nm. The width of the nanochannel can have a dimension of about 300 nm to about 1000 nm, or about 400 nm to about 800 nm, or about 500 nm to about 600 nm. The height/width can be the same to form a square nanochannel or the values may form a deep rectangle or a wide rectangle, or a circular or oval shape can also be used, with these dimensions being a diameter.

The pore can have various dimensions. The pore can be smaller than the rest of the nanochannel. The pore can have a length of about 50 nm to about 500 nm, 75 nm to about 250 nm, or about 100 nm to about 175 nm. The height/depth of the pore can have a dimension of about 100 microns to about 500 nm, or about 150 nm to about 450 nm, or about 200 nm to about 300 nm. The width of the nanochannel can have a dimension of about 50 nm to about 300 nm, or about 75 nm to about 200 nm, or about 100 nm to about 150 nm. The height/width of the pore can be the same to form a square nanochannel or the values may form a deep rectangle pore or a wide rectangle pore, or a circular or oval shape can also be used for the pore, with these dimensions being a diameter.

An example embodiment can include the nanochannel having a width and depth by length of about 500 nm by about 500 nm by about 15 microns. An example of the nCC can have a pore with about 200 nm width, about 200 nm depth, and about 100 nm length.

The microchannels can have various dimensions, such as a depth ranging from about 2 to about 25 microns, about 4 microns to about 15 microns, or about 10 microns. The height/width can be the same to form a square microchannel or the values may form a deep rectangle or a wide rectangle, or a circular or oval shape can also be used, with these dimensions being a diameter.

Figure 3B:
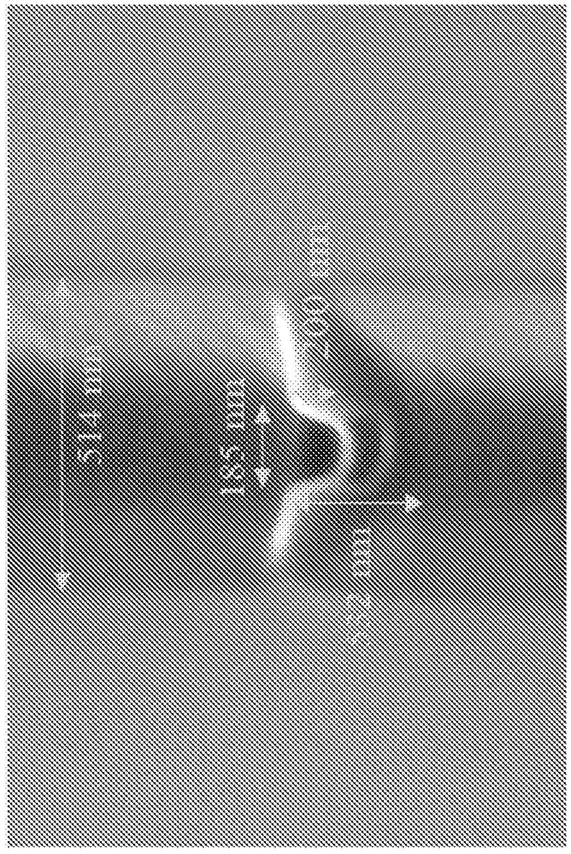
FIGS. 3A-3B include SEMs that illustrate an embodiment of a pore of a nCC.
Figure 3A:
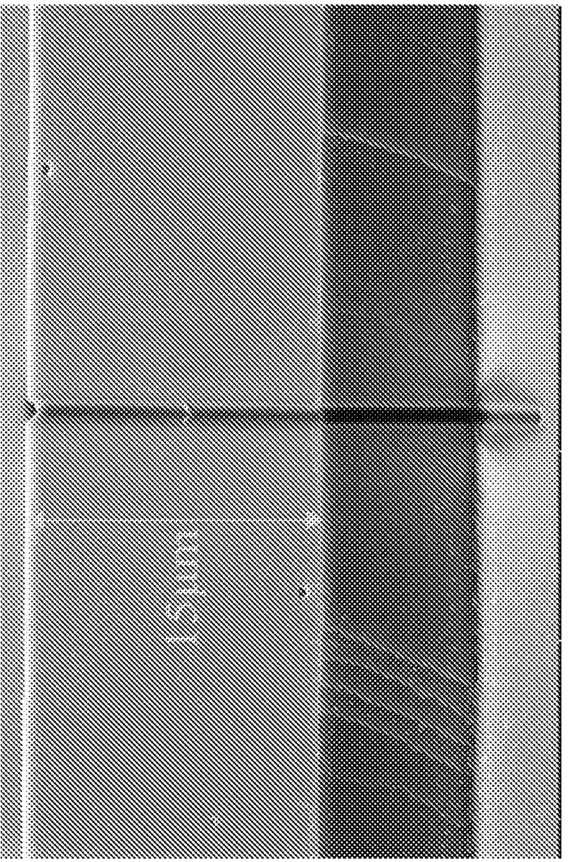

FIG. 2 shows the principle of how the in-plane nanopores in the example RPS generate signal when a particle passes through the pore. When the particle resides within the microchannel, no signal is generated. But, as the particle moves into the pore, a signal is generated because it occupies a part of the pore that causes reduction in the flux of ions passing through the pore. This subsequently reduces the current, which causes a peak (signal) to be generated. The sample was applied to one side of the microchannel while the other channel was filled with buffer and was connected to a syringe pump set to generate a withdrawing flow of about 20 μl/min. The other reservoir of this microchannel was sealed with epoxy to make sure the particles were primarily withdrawn from the sample microchannel and into the pore. The entire set up was connected to an amplifier circuit and a DC potential of −1 V was applied from the power source. FIGS. 3A-3B show SEM images of an example of the nanochannel and pore with a length of about 15 microns, nanochannel with a width of about 514 nm and depth of about 532 nm, and a pore having a length of about 200 nm, width of about 185 nm, and a depth of about 200 nm.

Figure 4A:
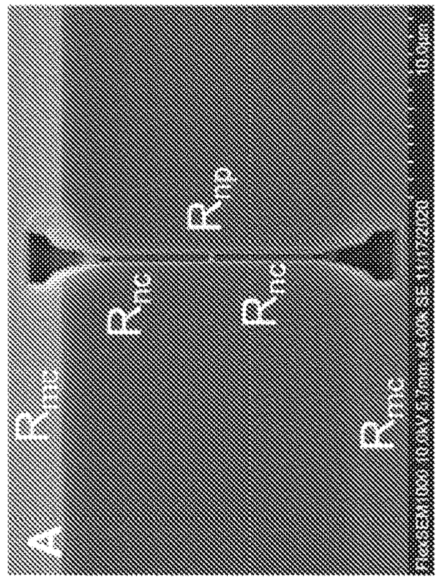
FIG. 4A includes an SEM of a pore of a nCC marked to show resistance parameters.
Figure 4B:
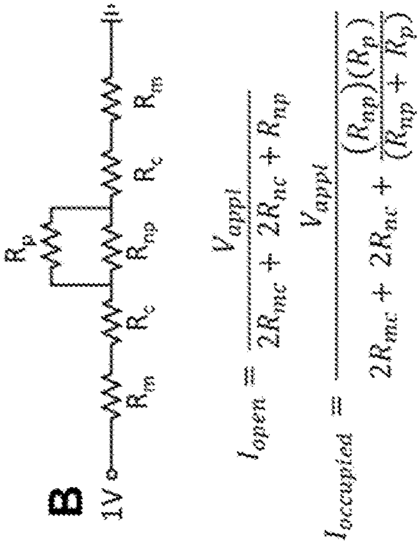
FIG. 4B includes a schematic diagram of the resistance parameter network of a pore of a nCC.
Figure 4C:
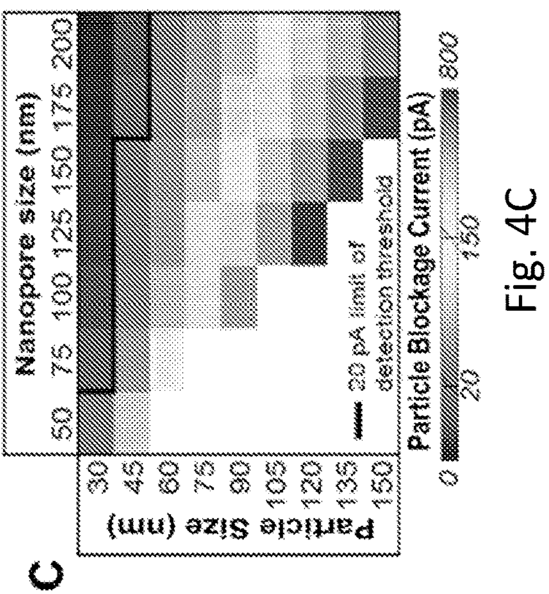
FIG. 4C includes a diagram that relates the pore size and particle size for relation with particle blockage current.
Figure 4E:
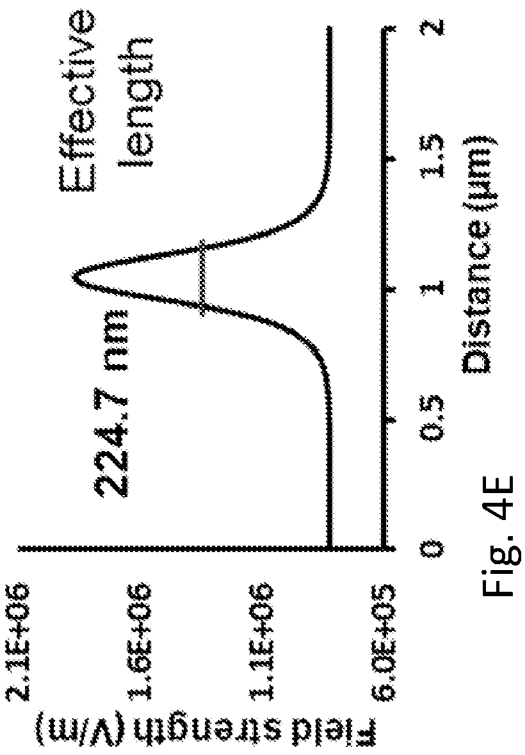
FIG. 4E includes a graph that shows the field strength versus distance to show the effective length.

FIG. 4A shows a SEM image of the example nCC having a 200 nm effective diameter. FIG. 4B shows the equivalent sensing circuit for the example nCC, where Rm is the resistance of the microchannel, Rc is the resistance of nanochannel, Rp is the resistance of the in-plane nanopore, and Rnp is the resistance of the nanoparticle. FIG. 4C shows the simulations of nanopore-based particle sensing showing the relation between the size of the particle and the size of the pore and the current drop that is expected. Also, COMSOL simulations of the voltage potential drop across the nanochannel were performed, as shown in the plot of potential drop vs. distance of nanochannel in FIG. 4D. The potential drop across the nanopore is only 4% in the 2D dimension. By involving the depth to the 3D factor, the nanopore only shares the potential by 10%. The electric field strength profile was obtained and analyzed, which showed the nCC having a higher field strength extending out to the nanochannel. FIG. 4E shows the graph that indicates 50% of full strength was taken as the effective nanopore length, which is about 224.7 nm.

Figure 4D:
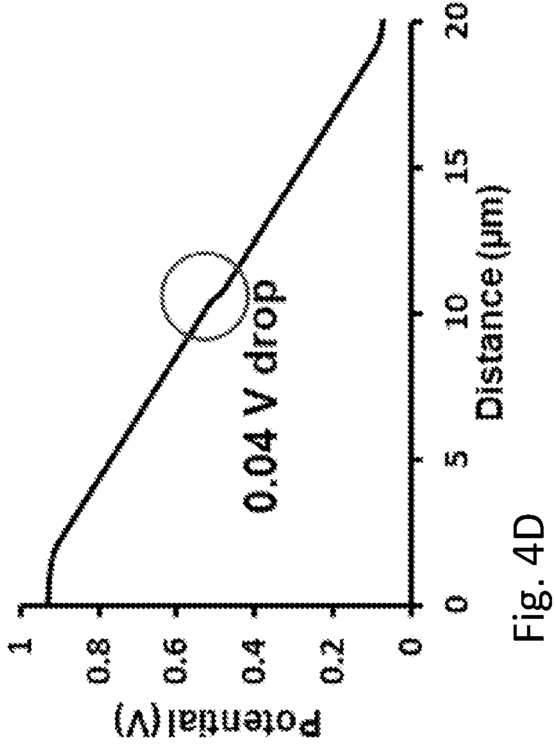
FIG. 4D includes a graph that shows the potential drop versus distance, which indicates the pore and its position.
Figure 4F:
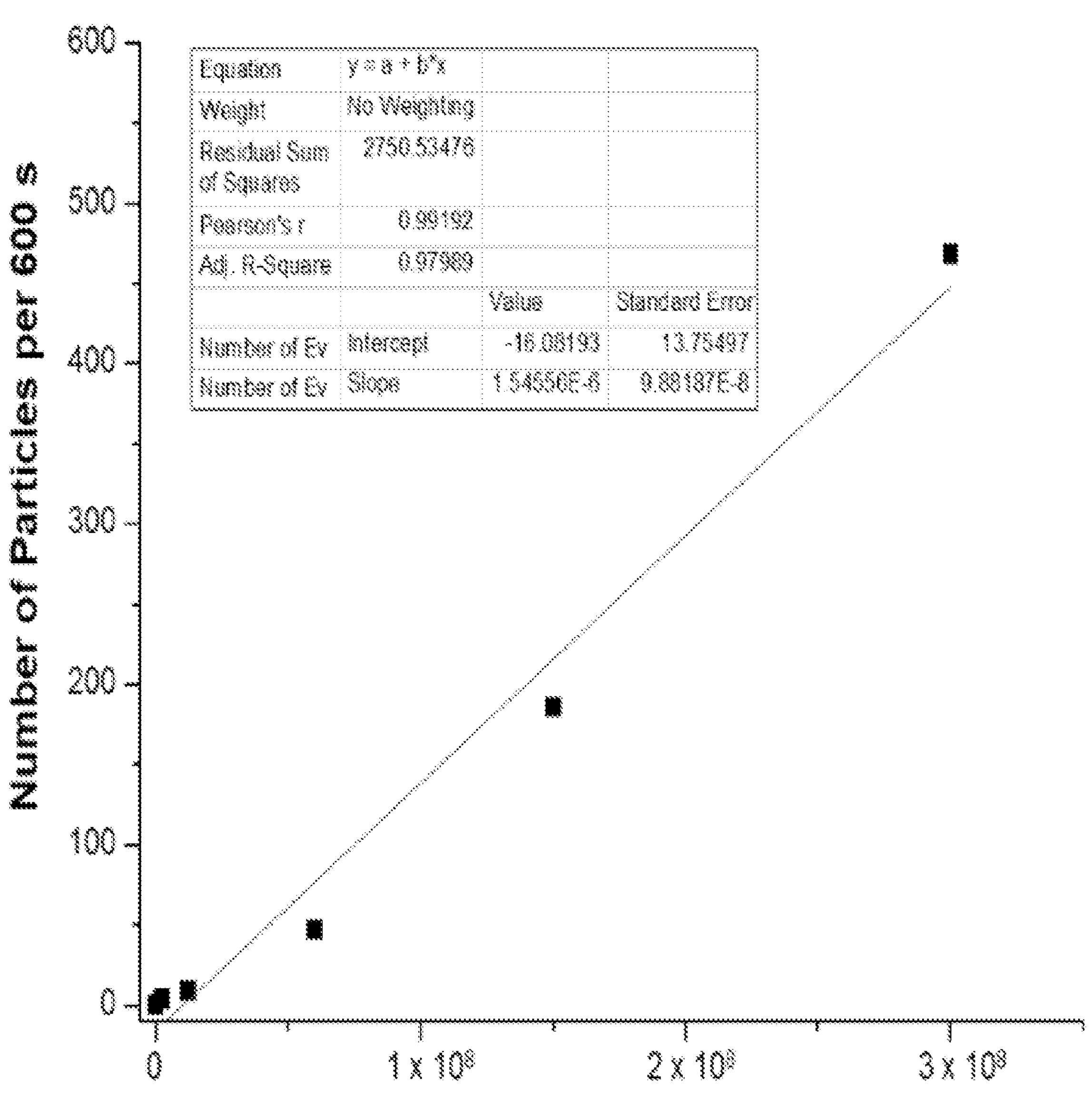
FIG. 4F includes a graph that shows the calibration curve for the number of particles counted versus the concentration of particles.

The resistance of the electrolyte in the device was considered as a series connection in the circuit. Whenever the particle is traveling through the in-plane nanopore, the particle forms a parallel resistor with the nanopore resistance. The experiment was modeled via COMSOL an in-nanopore as a fluidic constriction through which particles can pass and produce unique electrical signatures. When a particle occupies the nanopore, buffer ions are displaced; the nanopore's resistivity transiently changes and causes a detectable current transient event. Simulations aimed to gauge the feasibility (SNR) for enumerating 30-150 nm particles within 50-200 nm nanopores were carried out. Detectable current transient events were generated for all particles if nanopores were appropriately sized, and current spikes scaled cubically with particle size. Recorded peak amplitudes and widths can be used to determine the transit time of the particles within the sensing element. The pore size (~224 nm effective diameter) was predicated on optimizing the amplitude of the RPS signal with respect to the example SARS-CoV-2 particle size as determined using nanoparticle tracking analysis (NTA), which indicated an average diameter of ~143 nm. The line graph of the voltage shows that the majority of the potential drops across the nanochannel and nanopore with a sharp drop of 0.04 V across the pore as shown in FIG. 4D. The field strength graph in FIG. 4E shows a higher field strength at the nanopore due to its smaller dimensions with respect to the nanochannel and microchannels. However, the field strength extended out from the physical dimensions of the nanopore, thus increasing the effective length of the nanopore from about 100 nm to about 224 nm The number of peaks observed was correlated to the load concentration to establish a calibration curve from which the LOD could be determined (FIG. 4F), which shows the blank (1×PBS) trace that did not observe any events in a 30 s time interval. From this blank, a discriminator threshold condition was set so that no observable events would be registered in the blank to minimize false positive events when running the SARS CoV-2 samples. At a concentration of about $3\times10^8$ particles per mL, particles at about ~371 particles/μl were observed. When the sample was diluted by 100 fold, 21 particles/μl were observed. The calibration curve was generated and subsequently determined the limit of detection (LOD); the LOD is the lowest amount of sample that can be detected by an analytical procedure. In other words, LOD is estimated to be 3 times the standard deviation (SD) of the lowest concentration divided by the slope (m) of the calibration curve (LOD=3*SD/m). Based on the above criteria, the calibration curve showed that the concentration LOD was about $6\times10^5$ particles $mL^{-1}$ (600 s counting time) with a sampling efficiency, which is defined as the number of particles going through the single pore with respect to the number of particles traveling through the fluidic device, of about 4.5×10-4%.

Figures 5A, 5B, 5C:
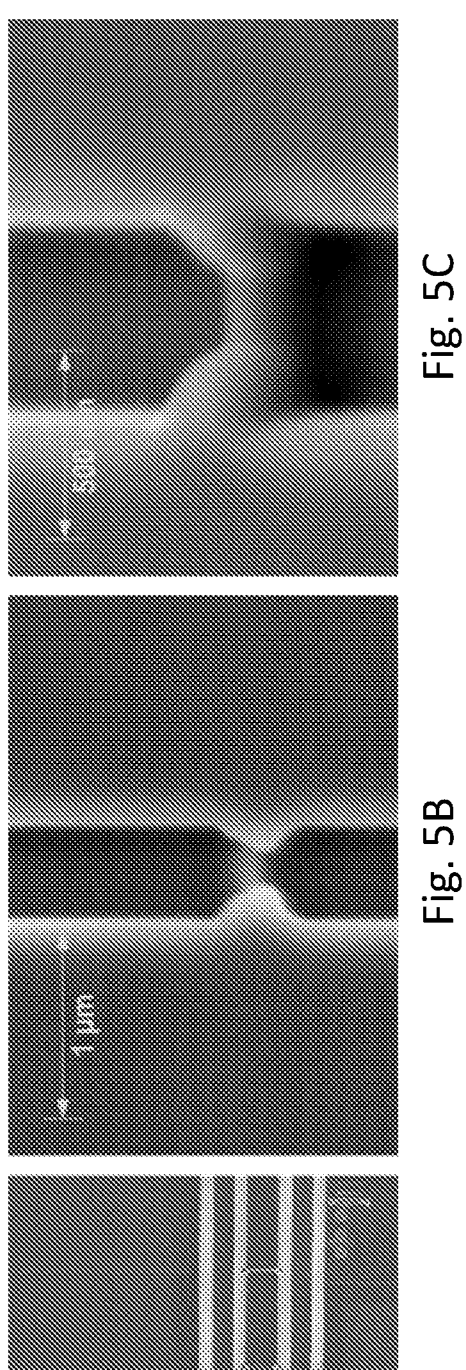
FIGS. 5A-5C include SEMs that illustrate an embodiment of multiple pores in a network nCC.

Additionally, a five pore design was tested, such as shown in FIG. 1. The pores were configured as shown in FIG. 2. FIGS. 5A-5C show the SEM of the five pore design, with one channel shown in FIGS. 5B-5C. The individual pores were fabricated with the same dimensions as compared to the previous single nanopore design (FIGS. 3A-3B and 4A-4F) and hence, the potential drop (0.04 V) as estimated for the single pore system, and as such, the effective pore length estimated from the electric field strength (~224.7 nm) in the individual pores remain the same. Although this design offered a higher sampling efficiency, the potential drop across the pore was only about 0.04 V.

Figure 6:
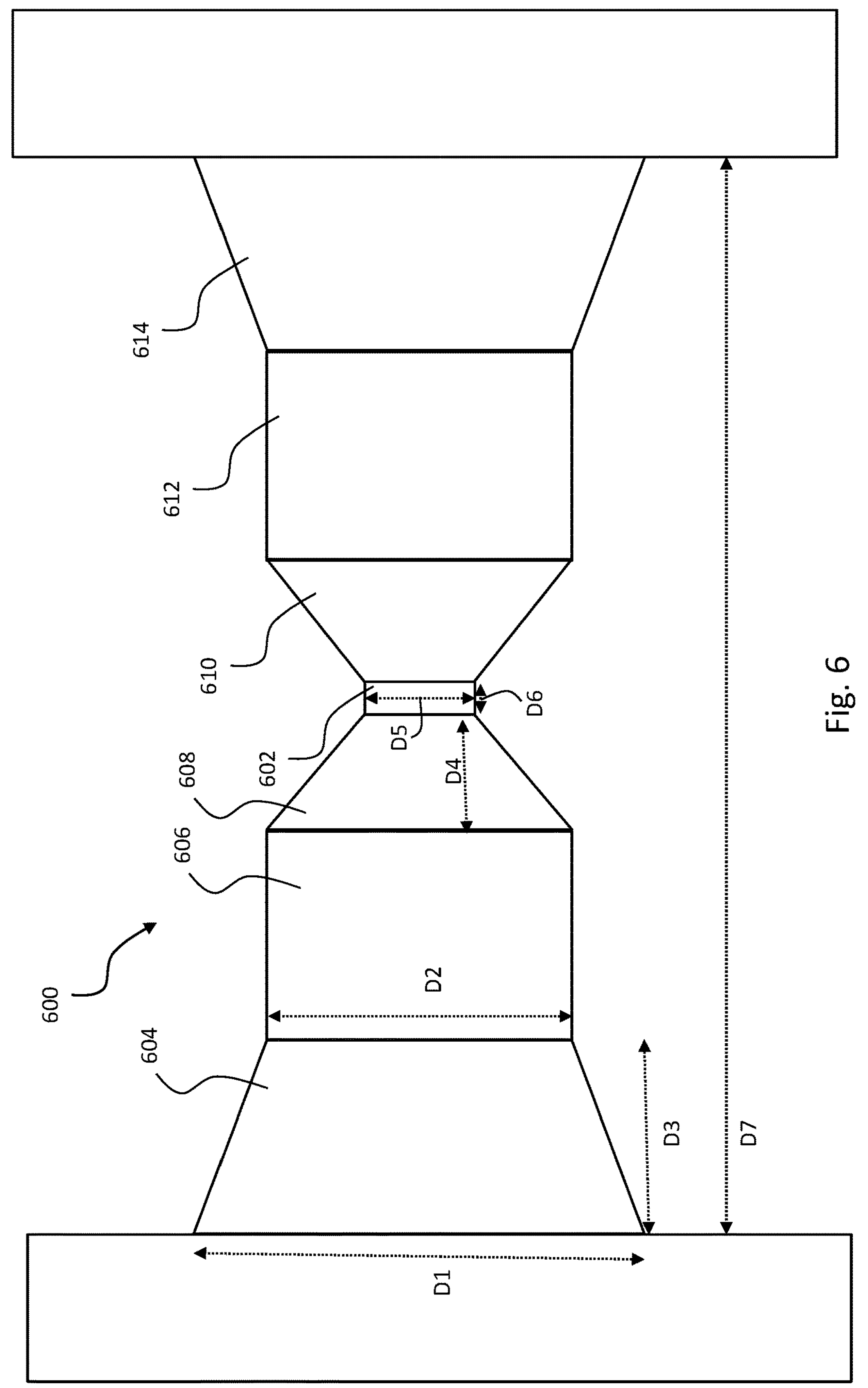
FIG. 6 illustrates an example of a nanochannel having a nanopore in a network nCC.

FIG. 6 shows another design of the nanochannel 600 with a pore 602 (e.g., nanopore). The nanochannel 600 has an opening dimension D1 of about 6 microns that tapers to a channel dimension D2 of about 2 microns, with an opening tapered region 604 having length D3 of about 3 microns. The channel 606 can have a channel width D2 of about 2 microns. The channel 606 has the channel dimension D2 for the width and a channel length of about 5 microns, which flows into an inlet pore tapered region 608. The inlet pore tapered region 608 can have an inlet of about 2 microns that is the same as D2, and an outlet taper of D5 of about 200 nm with an inlet pore tapper length D4 of 1 micron. The pore 602 can have the dimension D6 for a pore length, which is about 100 nm. The outlet pore tapered region 610, outlet channel 612, and outlet tapered region 614 mirror the corresponding inlet components. The entire length D7 can be about 18 microns Here, D1 can range from about 3 microns to about 9 microns, or about 4 microns to about 8 microns or about 5 micron to about 6 microns. The D2 can range from about 1 micron to about 3 microns, or about 1.5 microns to about 2.5 microns, or about 2 microns. The D3 can range from about 1 micron to about 9 microns, or about 2 microns to about 6 microns, or about 3 microns to about 4 microns. The D4 can range from about 2 microns to about 0.5 microns, from about 1.5 microns to about 0.75 microns, or about 1 micron. The D5 can range from about 100 nm to 500 nm, about 150 nm to about 300 nm, about 175 nm to about 250 nm, or about 200 nm. The D6 can range from about 50 nm to about 300 nm, about 75 nm to about 200 nm, about 90 nm to about 150 nm, or about 100 nm. The D7 can range from about 10 microns to about 50 microns, or about 15 microns to about 30 microns, or about 18 microns to about 25 microns.

Figures 7A, 7B, 7C:
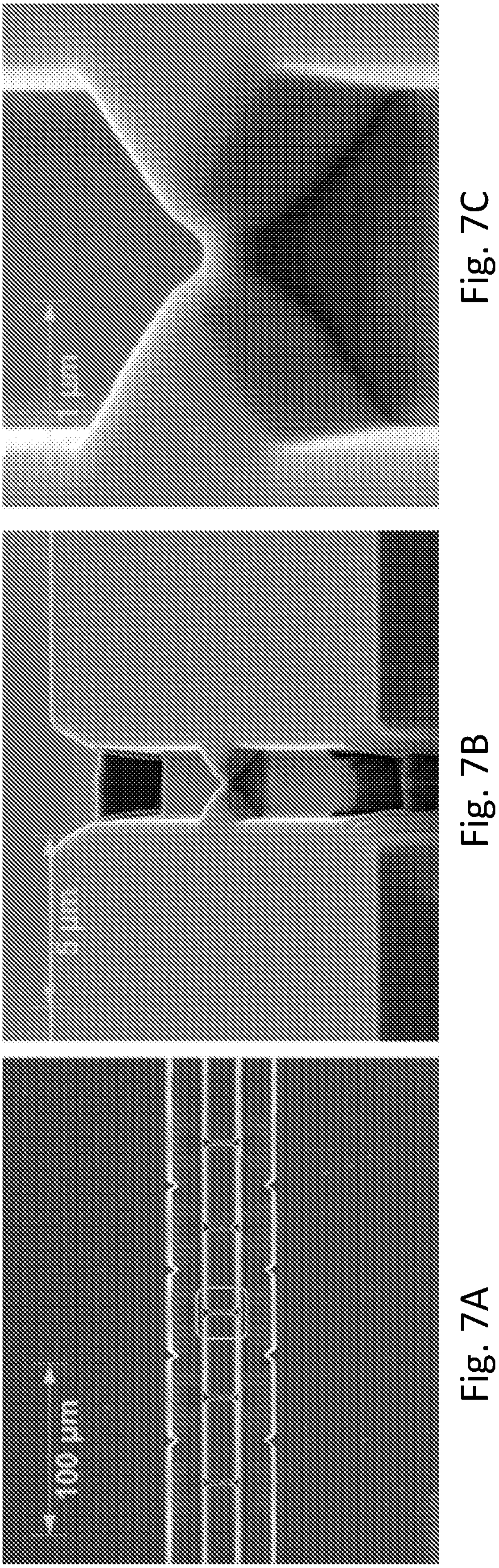
FIGS. 7A-7C include SEMs that illustrate the embodiment of multiple pores in a network nCC in accordance with FIG. 6.

The pore can be defined by the funnel structure as shown, which can be a 3D funnel. The funnel structure offers a more gradual increase in the electric field strength at the interface of the access microchannel to the in-plane pore, and also offered a higher sampling frequency of particles into the sensor. FIGS. 7A-7C show SEMs of the Si master with the five nanochannels, where FIGS. 7B and 7C show magnified images of the in-plane pores and the connecting microchannels.

Figures 7D, 7E, 7F:
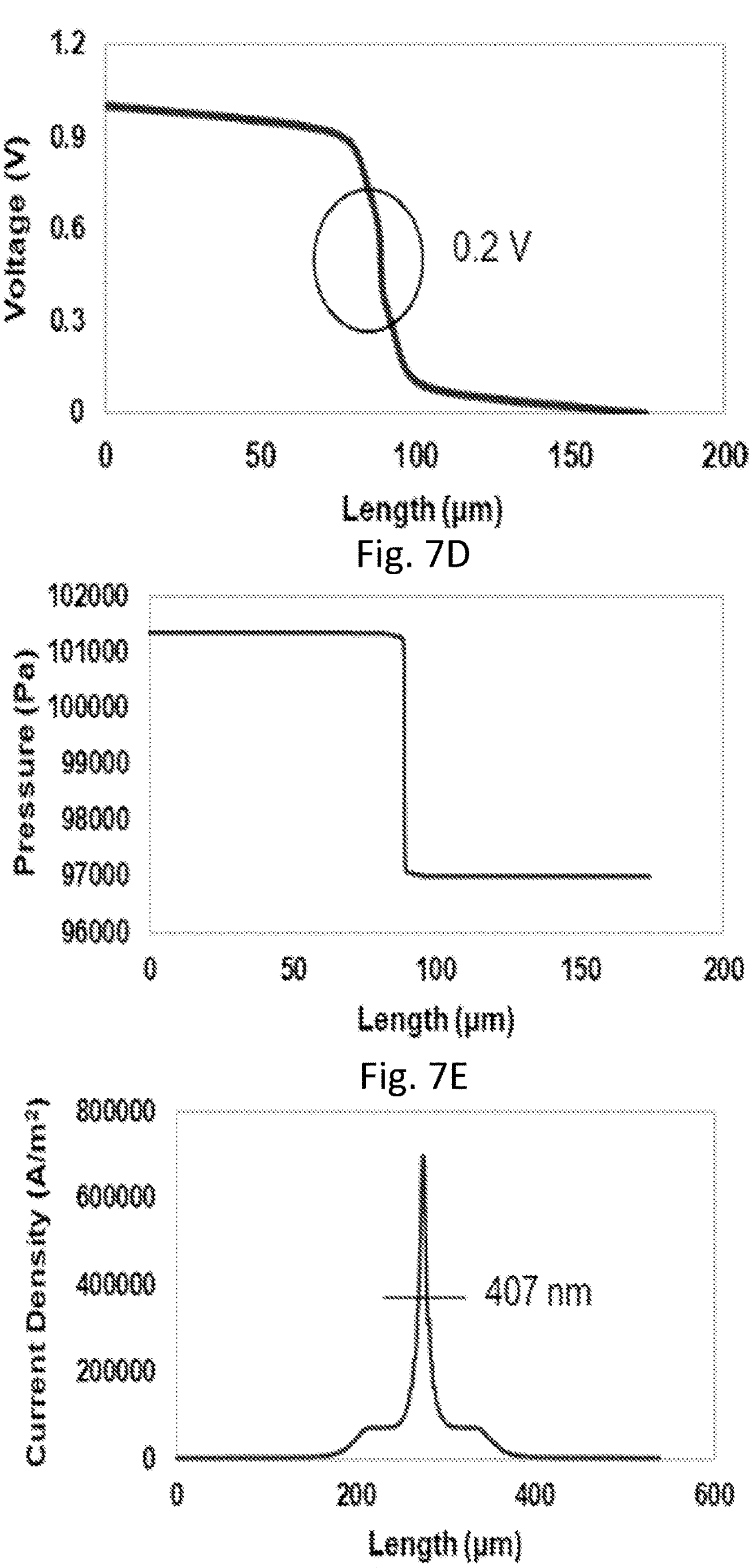
FIG. 7D includes a graph illustrating the voltage drop per length of the pore of FIGS. 7A-7C.
FIG. 7E includes a graph illustrating the pressure drop per length of the pore of FIGS. 7A-7C.
FIG. 7F includes a graph illustrating the current density per length of the pore of FIGS. 7A-7C.

In another example, a COMSOL simulation was performed with the nCC having five nanochannels configured as in FIG. 6. The velocity profile was obtained with the inlets set to atmospheric pressure on both inlets and the outlets set to 97000 Pa (estimated from the pressure sensor). The magnified image showing the higher velocity in the design. The pressure profile of FIG. 7E shows a sharp decrease in the pressure at the pore region. It is evident that a large pressure drop does not occur in the access microchannels or connecting channel. FIG. 7D shows the potential drop profile and a line graph showing the voltage drop at the pore (0.2 V) with the rest of the voltage drop occurring across the connecting channel. FIG. 7F shows the current density profile plotted from the voltage profile to estimate the effective length of the pore at FWHM, which is ~407 nm. This occurs due to the field strength extending out of the pore and into the connecting channel contributing to the current drop.

Accordingly, simulations for the nCC were based on a withdrawal rate of 20 μL/min resulting in a 3,000-4,000 Pa pressure drop across the in-plane pores. The pressure at the inlet was set to atmospheric pressure (101,325 Pa), while the outlets were set to 97,000 Pa for the simulation. COMSOL simulations of the velocity profile showed that there was fluid passing through all in-plane pores. The velocity in the access microchannels was found to be 1.5 mm/s, and in the pore regions the velocity increased to ~5 mm/s. With the increased size of the connecting channels, the potential drop in the pores increased from 0.04 V for the previous iterations to 0.2 V when 1 V was applied (FIG. 7D). The larger drop also increased the current density in the pore. Consequently, the effective length of the nanopore increased to ~407 nm increasing the effective sampling volume. The pressure drop profile of FIG. 7E, however, showed that the majority of the drop occurred only across the connecting channel and the in-plane pore region.

The selection chip (see FIG. 1) possessed a high-density array of micropillars coated with affinity-selection agents. The affinity-selection agents can be either monoclonal antibodies (mAbs) or aptamers, or others. When operated at about 20 μL/min, recovery of disease-associated EVs or viral particles is ~70%. The chip has a high surface area to accommodate loads >$10^{11}$ particles. The selected particles could be released from the affinity surface for particle enumeration using the nCC.

Figure 8:
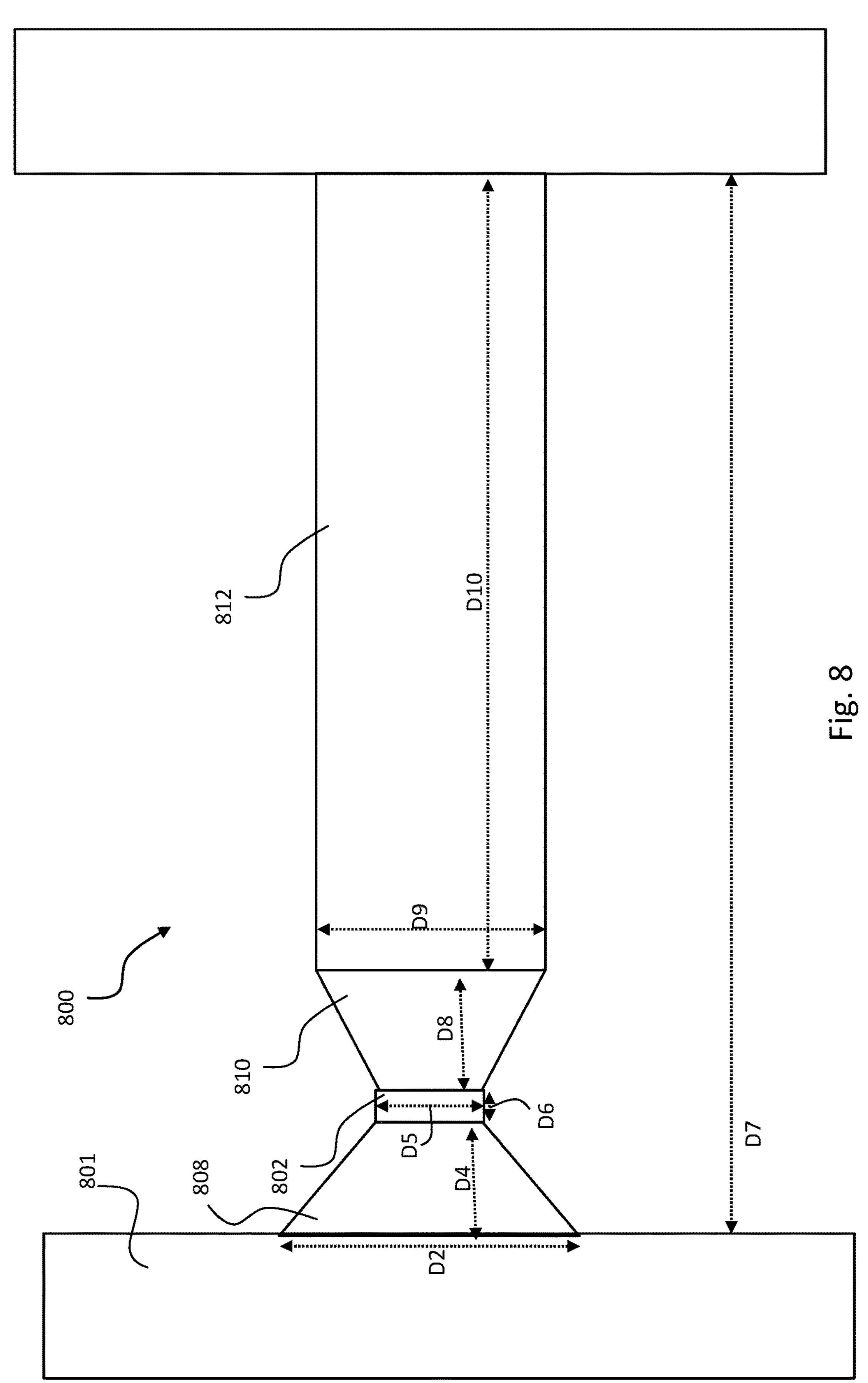
FIG. 8 illustrates an example of a nanochannel having a nanopore in a network nCC.

FIG. 8 shows another design of the nanochannel 800 with a pore 802. The nanochannel 800 has an inlet pore tapered region 808 directly from the feeder microchannel 801 that can have an inlet dimension D2 of 4 microns, and an outlet taper of D5 of 200 nm with an inlet pore tapper length D4 of 1 micron. The pore 802 can have the width dimension D4 and the length dimension D6 for a pore length, which is about 100 nm. The outlet pore tapered region 810 can have an inlet with a dimension D5, with an outlet dimension of D9 of 2 about microns with a length of D8 of about 1 micron (e.g., 0.8 microns). The outlet channel 812 can have a width dimension D9 of 2 microns and a length dimension D10 of about 18 microns. The entire length dimension D7 can be about 20 microns.

In some embodiments of the design of FIG. 8, D2 can range from 3 microns to 8 microns, from 3.5 microns to 6 microns, 3.75 microns to 5 microns, or about 4 microns. The D4 can range from about 2 microns to about 0.5 microns, from about 1.5 microns to about 0.75 microns, or about 1 micron. The D5 can range from about 100 nm to 500 nm, about 150 nm to about 300 nm, about 175 nm to about 250 nm, or about 200 nm. The D6 can range from about 50 nm to about 300 nm, about 75 nm to about 200 nm, about 90 nm to about 150 nm, or about 100 nm. The D7 can range from about 10 microns to about 50 microns, or about 15 microns to about 30 microns, or about 18 microns to about 25 microns. The D8 can range from about 0.5 microns to 2 microns, from about 0.75 microns to about 1.5 microns, or about 0.8 microns to about 1 micron. D9 can range from 1.5 microns to 4 microns, 1.75 microns to 3 microns, or about 2 microns to 2.5 microns. D10 can range from about 15 microns to 25 microns, about 17 microns to about 23 microns, or about 18 microns to about 20 microns.

The width of the access microchannels can range from about 25 μm (width and depth) to 10 μm or narrower (e.g., 2 μm), where narrower microchannels can increase the sampling efficiency. The in-plane pores in some embodiments can be placed in the center of the connecting nanochannels. However, in-plane pores in other embodiments can be directly coupled to the microchannel. For example, the pore can be downstream from a 3D tapered funnel at the feeding microchannel to further increase the sampling efficiency by extending the electric field further into the access microchannel. An SEM of the funnel and the nCC can be seen in FIGS. 9A-9C.

Figure 9A:
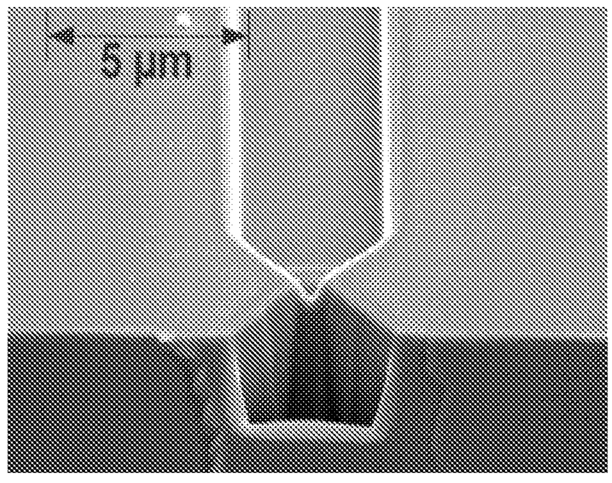
FIGS. 9A-9C include SEMs that illustrate another embodiment of pores in a network nCC in accordance with FIG. 8.
Figure 9B:
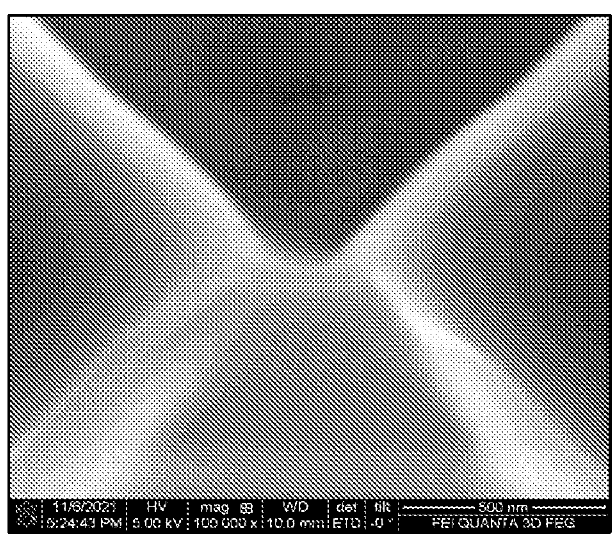
Figure 9C:
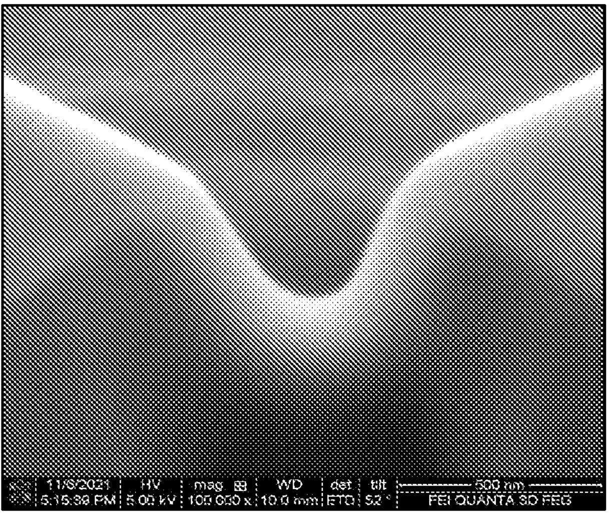

FIG. 9A shows a perspective view of the nanochannel showing the inlet pore tapered region narrowing to the pore than then expands at the outlet pore tapered region to the outlet nanochannel. FIG. 9B shows a top-down view of the inlet pore tapered region and outlet pore tapered region forming the pore 802. FIG. 9C shows a perspective view of the pore.

A nCC having five nanochannels 800 was studied in experiments using 1×PBS carrier electrolyte, the open pore current at 5 V applied across a single 350 nm ($d_{eff}$) pore was ~30 nA or 150 nA. From Ohm's law, the total resistance of a single 350 nm pore was determined to be 200 MΩ. For an average particle diameter of 150 nm, the occlusion volume, 0V ($V_p/V_{det}$; $V_p$=particle volume and $V_{det}$=effective pore sensing volume) is 2.8%. The potential drop occurs across the in-plane pore and the connecting channel (~4.8 V to 0 V), which is the channel region between the in-plane pores and the vacuum channel. The connecting microchannel (2 μm in depth and width) is 5.7 times greater in size than the 350 nm pore (see FIG. 8; SEMs of the fabricated device can be found in FIGS. 9A-9C). In this case, the electric field drop is fairly well restricted to the in-plane pore (see FIG. 9D). FIG. 9E shows the corresponding current density giving an effective length ($h_{eff}$) of 667 nm (FIG. 9F, 9G). Each pore gives a probe volume of 64.4 zL yielding a total volume for the 5 pores of 322 zL. The design length of the pores were about 100 nm.

Figure 9D:
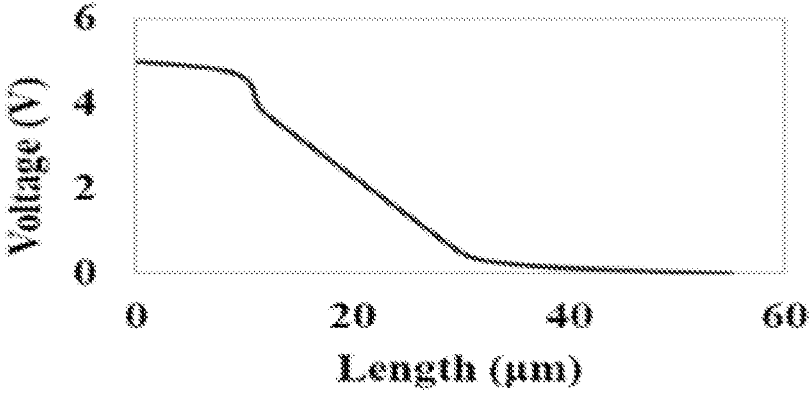
FIG. 9D includes a graph illustrating the voltage drop per length of the pore of FIGS. 9A-9C.
Figure 9E:
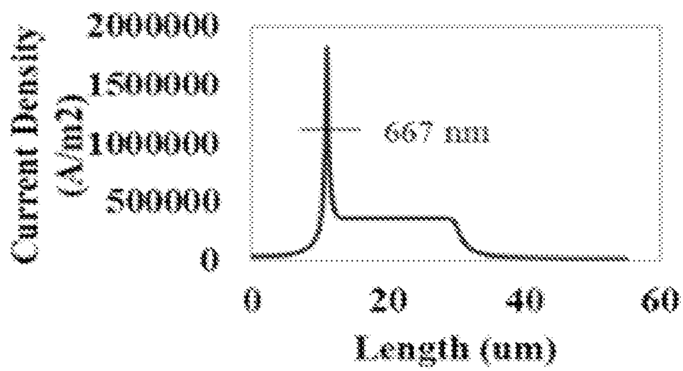
FIG. 9E includes a graph illustrating the current density per length of the pore of FIGS. 9A-9C.
Figure 9F:
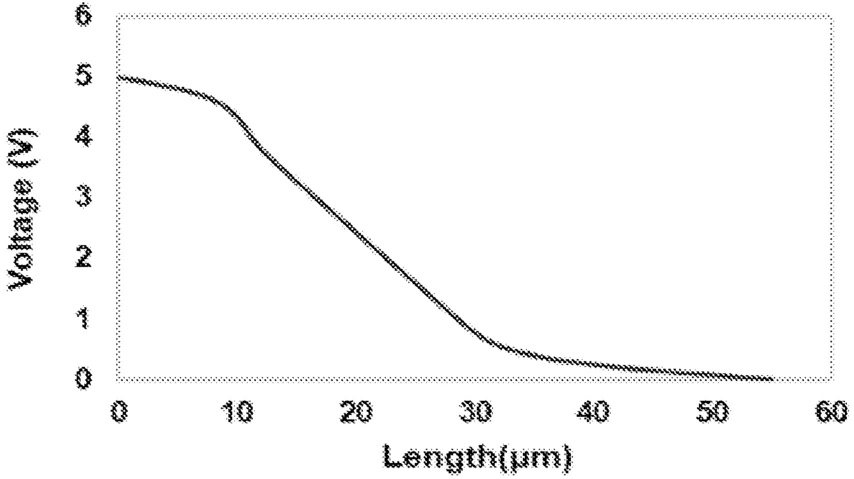
FIG. 9F includes a graph illustrating the voltage drop per length of the pore of FIGS. 9A-9C.
Figure 9G:
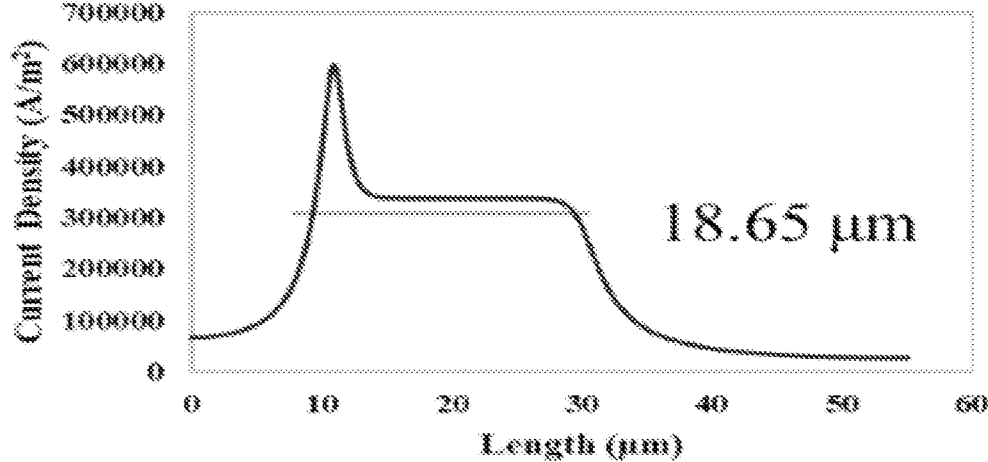
FIG. 9G includes a graph illustrating the current density per length of the pore of FIGS. 9A-9C.

FIG. 9D shows the COMSOL simulations of the 350 nm effective diameter pore showing the electric potential (−5V). FIG. 9E shows the COMSOL simulation of the current density corresponding to the potential drop with the regions in the nCC having a higher current density. Included is a magnified image of the nCC with the corresponding line plot of the current density. The current density plot of the nCC gave rise to an effective length of 667 nm. FIG. 9F shows the potential drop across the five nCC in-plane extended nanopore sensor. A 2-dimensional line plot of potential drop versus distance across one of the nCC in-plane extended nanopore sensors is shown in FIG. 9F. The potential drop across the nCC represents 10% of the total voltage drop across the sensor (5.0 V). FIG. 9G shows the current density profile plotted from the voltage profile to estimate the effective length of the pore at FWHM, which is 18.65 μm for a pore width of 1.75 μm.

The measurable signal, ΔI, could be estimated from $\Delta I \approx I_T \times OV$, where $I_T$ is 150 nA (open pore current for the 5-pore device and 1×PBS with V=5 V; 30 nA for each 350 nm pore). For a single 150 nm particle moving through either a single 350 nm pore in the 5-pore case device, ΔI would be 82.5 pA and a normalized amplitude response ($\Delta I/I_T$) of 0.55. Splitting the effective sampling volume for RPS into smaller pores (array of 5-pores in parallel) as opposed to a single larger pore can increase the signal-to-background ratio in the measurement. In addition, the net increase in volume throughput scales linearly with the number of pores in the array. Therefore, the selection of five pores in parallel was based on signal-to-background ratio considerations because a single amplifier circuit was used to sample the current transients produced by particles for the five pores simultaneously while at the same time increasing the volume throughput by a factor of five compared to a single pore device.

Figure 11A:
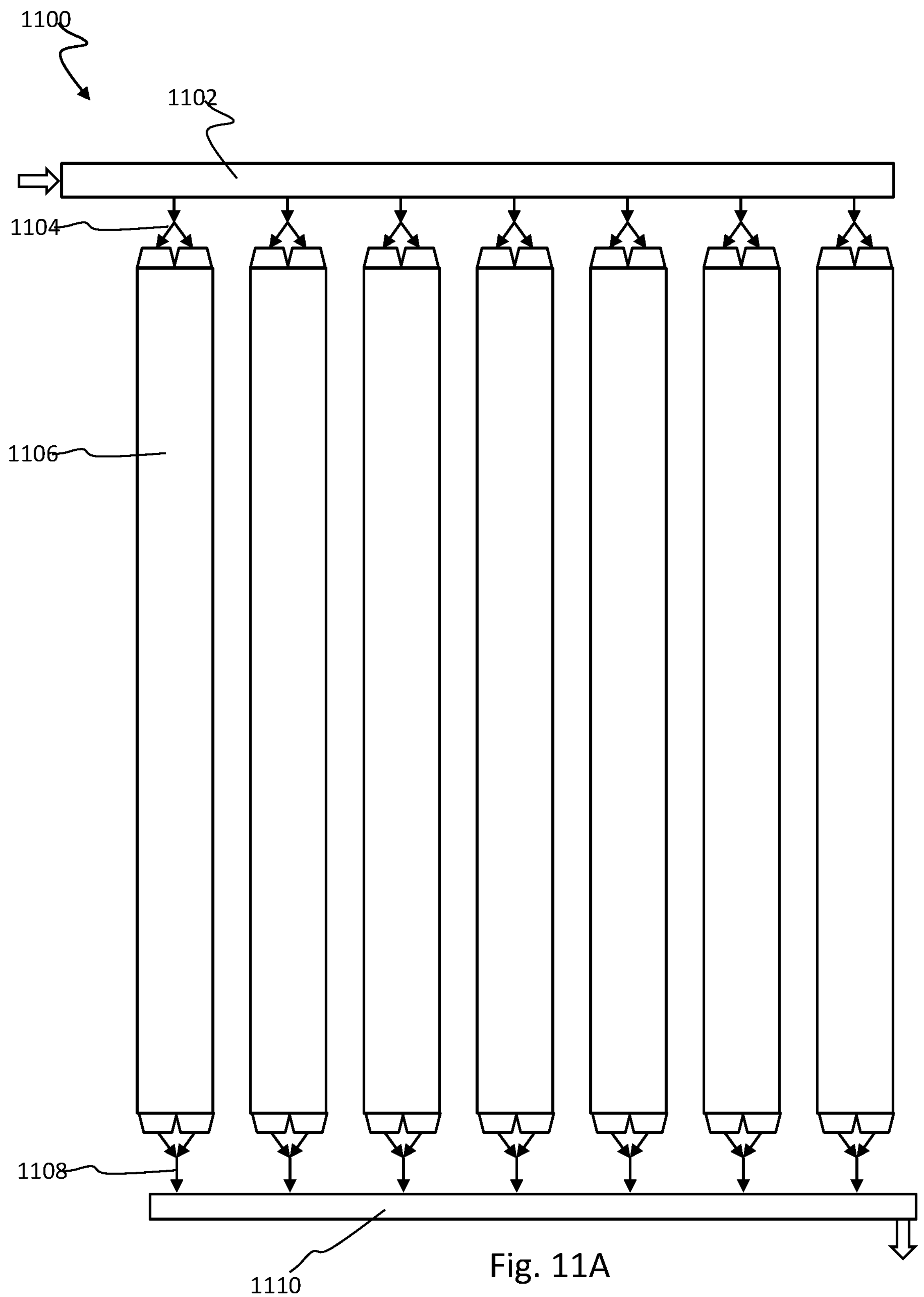
FIG. 11A illustrates a schematic diagram of an embodiment of a capture device in accordance with the present invention.
Figure 11D:
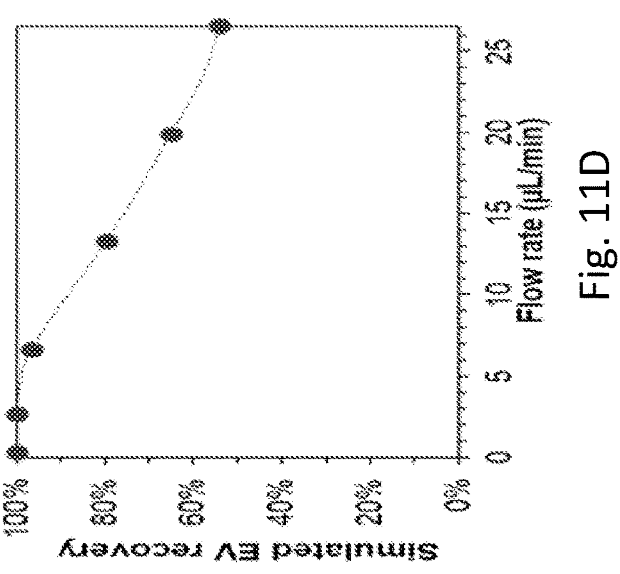
FIG. 11D includes a graph that shows the simulated extracellular vesicle (EV) recovery versus flow rate.
Figure 11C:
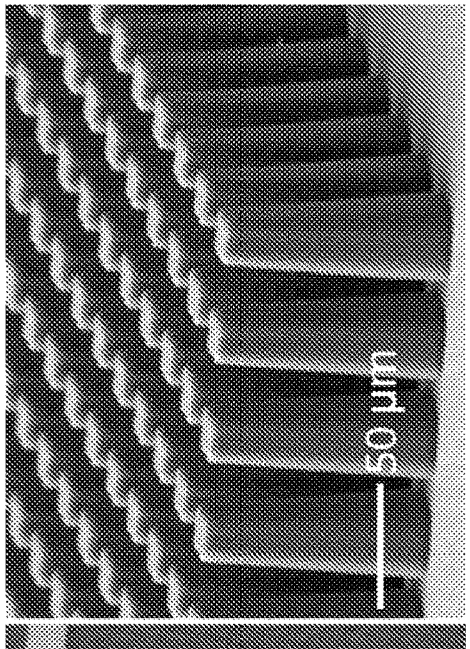
FIG. 11C includes a magnified image of the pillars of FIG. 11B.
Figure 11B:
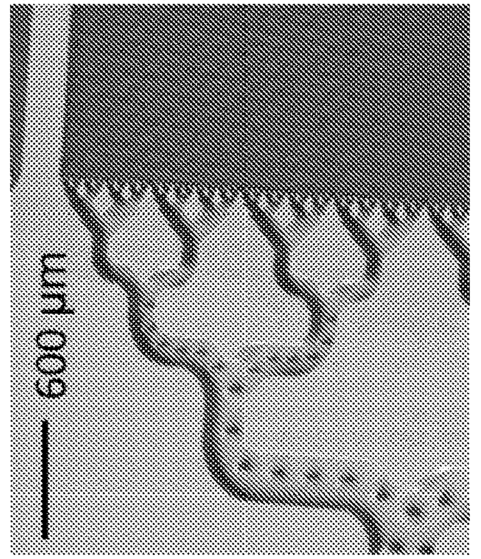
FIG. 11B includes an image of the fluidic network and pillars of the capture device in accordance with FIG. 11A.

FIGS. 11A-11C show an example selection device 1100. The selection device 1100 includes an inlet conduit 1102 connected through a distribution network 1104 to a pillar region 1106, which outlets to a combination network 1108 to an outlet conduit 1110. FIG. 11B shows an SEM of the distribution network that opens into the pillar region. FIG. 11C shows a SEM of the pillars of the pillar region. As shown, the number of pillars can be about 1.5 million (e.g., 1,475,712). The surface area of the bed with pillars can be 38.5 square centimeters. The internal volume can be about 35 microliters. The particle capacity can be about $1.1\times10^{10}$ particles. The pillar sizes can be about 10 microns square by about 50 microns tall. The pillars can be spaced about 10 microns apart. FIG. 11D shows the simulated recover of EVs with respect to flow rate.

In some embodiments, the operation of the nCC can be simulated, which can allow for tailoring unique characteristics for different types of particles to be detected. For example, COMSOL simulations can be used for the operation of the nCC. The simulations can be used to modify the parameters of the nCC.

In some embodiments, the nCC can be fabricated. The fabrication can be performed based on the simulations of the nCC. The fabrication of the nCC can include nano-injection molding to allow for high-scale production.

In some embodiments, the nCC can be fabricated using injection molding. The injection molding of the nCC device can be performed using resin-based mold inserts or Ni shims generated via electroplating from a patterned Si wafer. For example, a Si master can be obtained by fabrication using photolithography, dry etching, and focused ion beam (FIB) milling. Other techniques may be used.[43] The protocol can include a silicon dioxide wafer with a spin coating photoresist, which can be baked. Then, a photomask that allows passage of UV light therein in the shape of the features of the nCC is provided with UV light treatment. This provides the nCC microstructures in the material. Then, the photoresist is removed, and the silicon is etched. The silicon dioxide is removed to get silicon. Following formation of the microstructures, FIB is used for forming the nanostructures associated with the nCC. Micro/nano pattern transfers can be performed in three steps from the Si master to the stainless-steel block using PET substrates and two different resins. A stainless-steel block is prepared to include the resin stamp and the brass blank that are fit into the stationary and movable platens for injection molding. The resin mold inserts were used to allow injection molding to move through the various prototyping stages of the nCC development cycle. The use of the resin mold inserts allowed for the elimination of producing Ni mold inserts via electroplating. However, final production can use a Ni mold insert in place of the resin mold insert due to their higher robustness.

For example, the first step can include fabrication of a Si master using both photolithography and FIB milling. Then, a resin mold insert in MD700 or PUA was made using 2 transfer molds made in MD700. The final MD700 or PUA mold insert was built on a stainless steel block that could fit into the MUD of the injection molding machine.

The present nCC can have pores that are in-plane with a cyclic olefin polymer (COP) formed by nano-injection molding. Photolithography can be used to fabricate inlet/outlet access microchannels followed by focused ion beam milling (FIB) to produce extended nanopores (e.g., nCC) in a Si master. The features from the Si master can be transferred to COP through an intermediary UV-curable resin using the high-scale production technique of nano-injection molding.[38] The use of the intermediate resin stamp accommodated prototyping of several design iterations without requiring the production of metal molding tools via electrodeposition. The nCC can include any number of pores, where 5 parallel pores are provided herein by example, but can be 2, 3, 4, 5, 6, 7, 8, 9, 10, 15, 20, 25 or more.

In some embodiments, the nCC can be used for detecting a large range of different types of particles, from exosomes to viruses. For example, the nCC can be used for counting affinity selected SARS-CoV-2 viral particles from saliva samples. In another example, the nCC can be used for counting extracellular vesicles (EVs) selected from plasma samples of patients with ovarian or other forms of cancer. Therefore, the nCC can be configured for counting different types of particles.

In some embodiments, the nCC can be operated with a calibration curve up to a concentration detection limit. For example, a calibration curve was built to correlate the number of events detected using the five pore nCC with the concentration of particles, which yielded a concentration detection limit of about 2,500 particles/mL. This is a about 2,400-fold improvement compared to a single in-plane pore nCC device.

In some embodiments, the nCC can be used to distinguish certain types of desired target particles from background composition. Often, a particle that needs to be detected is in a sample. For example, the target particle can be SARS-CoV-2, which was detected with a positive reading from saliva samples following affinity enrichment using a microfluidic chip. In another example, EVs indicative of cancer may be distinguished from background sample, which shows the nCC can be used for discriminating between patients with high grade serous ovarian cancer from healthy donors using blood plasma as the input clinical sample. Thus, affinity selection followed by counting can provide for improved detection of target particles.

In some embodiments, the nCC can include nanopores. As defined herein, nanopores include dimensions <100 nm (effective diameter), while pores in the range of about 100-1,000 nm as used herein can be referred to as extended nanopores.[18] When a nanoparticle enters a three-dimensional constriction, the particle can displace a fraction of carrier electrolyte ions resulting in a measurable change in the pore resistance, which corresponds to a change in current ($\Delta I$). $\Delta I$ can be described using equation (1);

$$\Delta I = I_0 - V([\mu_+ + (1 - S)\mu_-]n_\pm e)\left(\frac{4h_{eff}}{\pi d_{eff}^2} + \frac{1}{d_{eff}}\right)^{-1} \tag{1}$$

In equation (1), the $I_0$ is open pore current (i.e., ionic current with no particle resident within the nanopore), V is the applied voltage, $\mu_+$ is the mobility of positive ions, $\mu_-$ is mobility of negative ions, $n_\pm$ is the number density of ions, $h_{eff}$ is the effective length of the pore, $d_{eff}$ is the effective diameter of the pore, and S is the fraction of excluded ions within the pore, which depends on the size of the particle.[19] We note that equation (1) is valid only for high salt concentration regimes in which the electrical double layer is compressed and thus shows minimal overlap within the pore.

Generally, RPS uses an electrolyte filled in the apparatus with electrodes placed on either side of the pore. One application of a potential across the pore, an electric current is generated due to the flux of ions moving through the pore where the electrical resistance is high and the large electric field drop across the pore. When an analyte moves through the pore, it causes a transient increase in resistance, which causes a drop in current. Depending on the size of the particle the change in resistance as a spherical particle passes through a cylindrical orifice is given by the following equations:

Equation 1.1

$$\text{Infinitely small diameter particle: } \frac{\Delta R}{R} = \frac{d^3}{D^2 L}$$

Equation 1.2

$$\text{Smaller diameter: } \frac{\Delta R}{R} = \frac{d^3}{D^2 L}\left[\frac{D^2}{2L^2} + \frac{1}{\sqrt{\left(1 + \left(\frac{D}{L}\right)^2\right)}}\right] F\left(\frac{d^3}{D^3}\right)$$

Equation 1.3

$$\text{Medium diameter: } \frac{\Delta R}{R} = \frac{d^3}{D^2 L} \cdot \frac{1}{1 - 0.8\left(\frac{d}{D}\right)^3}$$

Equation 1.4

$$\text{Large diameter: } \frac{\Delta R}{R} = \frac{D}{L}\left[\frac{\arcsin\left(\frac{d}{D}\right)}{\sqrt{\left(1 - \left(\frac{d}{D}\right)^2\right)}} - \frac{d}{D}\right]$$

Here, D and L are the diameter and length of the sensing orifice, d is the diameter of the particle, and $F(x)=1+1.264x+1.347x^2+0.648x^3+4.167x^4$. The equations mentioned above use particles and sensing orifices of different sizes. The small diameter equation represents d ranging from 60 nm-357 nm with a D of 490 nm. The D*, which is defined as (d/D) ranges from 0.122-0.728 in this case.[58] In case of the medium diameter, the particles typically used were 91 nm and 109 nm in orifices of 324 nm and 252 nm giving a D* of 0.34 and 0.36, respectively.[59] However, the larger diameter equations were developed when 2.5 cm disks were sensed using 5 cm orifice (D*=0.5).

In some embodiments, the nCC can be configured to detect biological particles having diameters ranging from 40-350 nm (average ~150 nm). The nCC can be configured to have a sufficient concentration LOD to span the entire clinical concentration range required for biological nanoparticle measurements. Therefore, a nCC can have a pore diameter as desired for the target particle to be detected. For example, SARS-CoV-2 viral particles in clinical saliva samples can range from 500-108 viral particles per mL.[38] In some aspects, the nCC can be prepared via nanoimprint lithography in COP to have a concentration LOD of $5.8\times10^6$ particles per mL.[39] For improved LOD, the nCC device can include a higher number of pores, such as five pores in parallel, to increase the sampling efficiency to allow for the detection of particles even at low concentrations. In some aspects, the nCC can be prepared from thermoplastics in order to fabricate nanopores of ~350 nm in effective diameter to detect single particles (e.g., virus) with an average size of ~150 nm.

The nCC can be optimized using COMSOL simulations. Measurements can be conducted to verify simulation results. The nCC device has been shown to be effective in two applications, as described herein: (1) saliva COVID-19; and (2) ovarian cancer EVs. In the first example, saliva samples of both COVID-19 negative and positive patients were subjected to affinity purification using a microfluidic chip, the enriched SARS-CoV-2 particles released from the chip and then counted using the nCC device to determine disease status. In the second example, EVs were affinity selected from plasma samples of patients with ovarian cancer. In both applications, the biological particles were surface affinity selected using a pillared microfluidic chip[40] followed by release of the surface-captured particles using a photocleavable linker[41] and subsequently enumerated using the nCC.

In some embodiments, the nCC can be a microfluidic device having a micropore with a nano-Coulter Counter for use in detecting particles. The present innovative technology described herein has been invented to directly addresses the following issues: the present technology can be performed without reagents (e.g. enzymes, fluorescent reporters, antibodies); the present technology has simplified workflows that do not require specialized operators; the present technology can distinguish between infectious and non-infectious samples, and thereby provide indications of individuals being contagious or non-contagious, which is important in determining the time for quarantining.

In an example viral particle detection program, the technology specifically selects active SARS-CoV-2 particles from a clinical sample using surface-immobilized DNA aptamers targeting the spike protein. Then, the surface immobilization of the DNA aptamers is cleaved by light, which releases (e.g., photolytically) the selected viral particles (VPs). Then, the counts of the number of SARS-CoV-2 particles is performed using a label-free approach with the nCC pores. For example, the label-free approach to counting the particles can be via resistive pulse sensing (RPS), as described herein. The workflow is simple and fully automated, which can be controlled with a computing system configured as a controller. Additionally, no reagents are required.

In some embodiments, the particle selection chip can include 1.5 million pillars that allows for affinity loading or approximately ~$10^{10}$ SARS-CoV-2 particles at a recovery of 94.3%. Following selection, the particles are released from the capture surface using a photocleavable linker by a blue-light LED (89% release efficiency) and subsequently counted using a nCC. However, it should be noted that a suitable affinity selection of any type of virus particle, or any other type of particle (e.g., EV), can be performed without limitation, and thereby other types of particles can be detected.

In some embodiments, a system is provide for detecting viral particles. The system can include a microfluidic network having a biological sample inlet. The system can include at least one surface-bound affinity-selection agent (e.g., antibody, aptamer, etc.) in the microfluidic network. In an example, the aptamer sequence selectively binds the ACE2 receptor binding domain of an S-protein of the SARS-CoV-2 viral particle. For example, the pillars described herein can be coated with the affinity-selection agent. In another example, a surface-bound aptamer can includes an aptamer sequence that binds with a target motif on the particle. Also, the surface-bound affinity-selection agent includes a stimulus-responsive cleavable linker. The system can also provide a means for providing a stimulus to the surface-bound aptamer. In some aspects, the stimulus can be light (e.g., blue LED), and thereby the system can include a light emitter that can emit light to release particles bound to the affinity-selection agent.

The selection device can include the means for providing the stimulus that cleaves the stimulus-responsive cleavable linker. The means can be selected from the group consisting of: a chemical input means, wherein the chemical cleaves the linker; light input means, wherein light cleaves the linker; sound input means, where sound cleaves the linker; heat input means, wherein heat cleaves the linker; or combinations thereof. The selection device can include an optical aperture as the light input means, wherein the optical aperture allows light to pass therethrough that photolytically cleaves the linker.

The detection system can also include a microfluidic network that includes a plurality of nanochannels having a plurality of micropores that are downstream from the surface-bound affinity agents. The microfluidic network includes a microfluidic channel having an inlet diameter and an outlet diameter, and a micropore therebetween. Each micropore can be configured as a nCC with an inlet, a pore, and an outlet, with an electrode pair that can cause flowing of ions in a media in the device. In some aspects, at least five micropores are included in the nCC. The nCC can include a current amplifier is configured for the counting of the particles as described herein. The nCC is configured as a resistive pulse sensing (RPS) device to detect individual viral particles. The system can include a DC current supply operably coupled with the nCC, such as an electrode pair for each fluidic network or for each nanochannel/nanopore.

In some embodiments, the nCC includes a narrow channel configured for electrically detecting individual particles, the channel cross-dimension (e.g., width, depth, diameter) being greater than about 150 nm and smaller than about 1000 nm, smaller than about 750 nm, smaller than about 500 nm, smaller than about 400 nm, or about 350 nm. The microfluidic network includes at least one microfluidic channel having an inlet diameter of greater than about 200 nm and an outlet diameter greater than about 200 nm, and a micropore therebetween with a diameter of about 200 nm or less and a length of about 100 nm or less. In some aspects, the microfluidic network includes at least one microfluidic channel having a taper from the channel lumen to the micropore lumen. In some aspects, a pump is operably coupled with the microfluidic network.

In some embodiments, the nCC can include at least one camera operably coupled with the microfluidic network. The one or more cameras can be upstream of the pore, at the pore, or downstream from each pore.

In some embodiments, the system can be configured for measuring pressure at one or more locations in the microfluidic network. For example, a pressure sensor can be located upstream or downstream from each micropore, or at each micropore.

In some embodiments, the system can include a controller for controlling operation of the system as well as obtaining operational data. For example, the controller can control the power source and control the measurement of the current in the system. The controller can be operably coupled with the means for providing the stimulus that cleaves the cleavable linker, and thereby the stimulus is controlled. The controller can be operably coupled with the nCC such that the particles are counted. The controller can also be operably coupled with the pump that is operably coupled with the microfluidic network in order to control fluid flow therein.

In some embodiments, a method of detecting a particle in a sample is provided. The method can include providing a biological sample from a subject. The biological sample can be contacted to a surface-bound affinity-selection agent in a microfluidic network. The affinity-selection agent binds with a target motif on the particle. The affinity-selection agent is bound to the substrate via a photolytically cleavable linker. The target particle can be captured with the affinity-selection agent. The particle can be released by photolytically cleaving the linker. The particle can then flow through the nCC system where the number of particles that are released are counted.

In some embodiments, a method of detecting a particle in a sample can include providing a biological sample from a subject. The biological sample can be provided to a microfluidic system having to a surface-bound affinity-selection agent in a microfluidic network linked by a stimulus-responsive cleavable linker. The particle can be captured by the affinity-selection agent, and then released by providing the stimulus that cleaves the stimulus-responsive cleavable linker. The number of particles that are released are then counted. In some aspects, the viral particle is a SARS-CoV-2 and the aptamer sequence binds with the target motif of the SARS-CoV-2 viral particle. In some aspects, the stimulus that cleaves the stimulus-responsive cleavable linker is selected from the group consisting of: chemical, wherein the chemical cleaves the linker; light, wherein light cleaves the linker; sound, where sound cleaves the linker; heat, wherein heat cleaves the linker; or combinations thereof. In some aspects, the stimulus is light, and the photolytically cleavable linker is cleaved by light in the blue spectrum. In some aspects, the microfluidic network includes a plurality of pillars having the surface-bound aptamer.

Once the particles are released, the flow out of the selection device and into a nCC device. The method can include passing the released particles through a plurality of in-plane micropores in parallel and counting via electrical detection via the RPS protocol.

When the particle is a viral particle, then the method can include determining the presence of the viral particle based on the capture/release and count of the nCC. This can be used to determine that the subject that provided the biological sample has active virus (e.g., COVID-19), and defining the subject has being contagious. The method can include detecting viral particles at a concentration as low as being greater than or about $10^3$ particles/mL.

In some embodiments, the determination of the subject being infected with a virus can be validated. The validation can include obtaining a nucleic acid from the released viral particle. Then, a RT-qPCR can be performed on the nucleic acid, and the identity of the viral particle can be confirmed from the RT-qPCR. Thus, the method can include determining the type of viral particle from the RT-qPCR. For example, the method can include determining the viral particle to be SARS-CoV-2 viral particle.

In some embodiments, the detection methods can include at least one of the following: modulating fluid flow rate and/or pressure in the microfluidic network; imaging the particles in the microfluidic network; or modulating electrical potential across the nanopores.

In some embodiments, the methods can include providing a report that includes a determination of whether the particle is present based on the counted particles. The report can include a determination of whether the particle is present based on the captured/released counted particles.

EXAMPLES

Silicon masters were prepared by using a combination of photolithography and wet-chemical etching to make microstructures followed by FIB milling to generate the nanostructures. Photolithography was accomplished by spin coating AZ 9260 positive photoresist onto a $SiO_2$ wafer (p-type, resistivity 5 $\Omega cm^{-1}$) at 4,000 RPM for 60 s. The $SiO_2$ wafer was spin coated with AZ 9260 photoresist and post-baked at 100° C. for 5 min. After post-baking, the microstructure patterns from the optical mask were transferred onto the resist layer by exposing it to UV light (25 mW/cm$^2$) for 24 s and developing it with MIF 200 developer. The patterned surface was exposed to a buffer oxide etch (BOE) solution to remove selected regions of the $SiO_2$ and the photoresist layer was then removed using acetone. The underlying Si was subsequently etched using a 40% KOH solution. The top oxide layer was then completely removed with BOE solution. Finally, nanostructures were fabricated using FIB milling (Quanta 3D Dual Beam system, FEI). The milling was performed at a beam voltage and current of 30 kV and 10-50 pA, respectively, in a bitmap writing mode.

The UV resin mold insert on a stainless-steel block was prepared. The patterns in the Si master were transferred to a UV-curable resin (a mixture of 97 wt % MD 700 (Solvay Solexis, Italy) and 3 wt % Darocure 1173 (Sigma Aldrich)). Drops of the UV resin were dispensed onto the surface of the Si master. A flexible polyethylene terephthalate (PET) sheet coated with an adhesive layer (NOA72, Norland Products) was then gently pressed against the liquid drop. During the curing process, the sample was exposed to UV light (365 nm) for 3 min at 30 mW/cm$^2$ using an ELC-500 UV curing system (Electro-Lite). The positive toned features on the first MD700 resin stamp were inverted compared to those within the Si master. These patterns were then used to form a second MD700 resin stamp with negative toned features using a second PET back plate using the same UV curing process as described previously. For the final step to create the resin-based mold insert, the top surface of a stainless-steel block was polished, treated with $O_2$ plasma at 50 W for 2 min and coated with an NOA72 adhesive. Then, UV resin stamps (MD700) were produced on the metal block using the negative toned MD700 resin stamp. After demolding, positive toned UV resin stamps were formed on the metal block and used for injection molding.

The injection molding machine (Arburg 307A) was equipped with a master unit die (MUD). One side of the frame was movable and fitted with a brass blank insert having a cavity where the polymer is filled. The other frame is stationary and fitted with the stainless-steel metal block with the UV resin stamp. In a general sequence of injection molding steps, the process started with the mold closing followed by molten polymer flowing into the mold cavity through a nozzle. After packing the molten polymer under a hold pressure of 800 bar for 2 s, the thermoplastic was cooled for a fixed time and the injection molded device was ejected by ejector pins. Following injection molding, the nCC chip containing the fluidic network (i.e., substrate) was thermally fusion bonded to a cover plate, which consisted of cyclic olefin copolymer (COC) 8007, which has a $T_g$ (glass transition temperature) lower than the COP substrate (Zeonor 1020R®, $T_g$=102°). The bonding of a low $T_g$ cover plate (83°) to a higher $T_g$ substrate (102°) minimizes molded structure deformation and improves the process yield rate (>90%) as opposed to using the same material for the cover plate as that used for the substrate.[44] The COP chip was covered with a thin COC cover plate with both treated using an $O_2$ plasma for 2 min and thermal fusion bonded at 72° C. and 0.83 MPa for 15 min.

The nCC was prepared in two different materials; (i) polymethyl methacrylate (PMMA) and (ii) cyclic olefin polymer (COP) to evaluate if nanoparticles adsorbed to the channel walls. Polystyrene Nile red beads (40 and 100 nm) at a concentration of about $10^6$ particles/mL in 1 M NaCl and 1×PBS were introduced into the device, while 1×PBS only was filled on the buffer side and was withdrawn at a flow rate of about 20 μL/min. The device was filled and placed on a wide-field epifluorescence microscope having a 532 nm laser equipped with a 60× and 100× oil immersion objective and a sCMOS camera. The data showed Nile red beads adsorbed to the surface of a PMMA device, while in the case of COP, the beads did not seem to stick. Beads were also seen to move through the in-plane pores using a withdrawal rate of about 20 μL/min, but with low sampling efficiency. Thus, COP can be preferred for the material for the components of the system, such as the microfluidic network, pillars, and nCC.

In an example, the bias voltage on the nCC device was set to 1 V and particle concentration (heat inactive SARS-CoV-2) was about 52,000 particle per mL with a counting interval of 100 s. It was found that the maximum event frequency with the conditions used here was found to be 1 μL/min. The data can have a baseline subtracted and filtered using a 400 Hz high pass filter. The sampling frequency can be set to 100 kHz.

The 100 kHz sampling frequency was ~33-fold larger than the inverse peak full width half maximum (FWHM) value. We adopted a threshold condition for the amplitude of the events to be 5× the standard deviation of the open pore current as this eliminated false positive results. A 10 kHz filter had a SD of ~11 pA and a 5 kHz filter had a SD of ~6 pA. With the SD noise levels at 10 kHz being reasonable (event threshold of 55 pA at 10 kHz, and 30 pA at 5 kHz), we selected 10 kHz as our filter. These parameters may be varied herein within the skill of one of ordinary skill in the art, such as by up to 1%, 5%, 10%, or 20%

Overall Experimental Set Up with Current Amplifier Circuitry

In some experiments, about 5 μl of sample is filled on the inlet microchannel and a drop of sample is placed on either ends of the reservoir. The outlet channel is filled with 1×PBS as the buffer. One end of the outlet is sealed with epoxy, while the other end is connected to a syringe pump that withdraws fluid at 20 μl/min. A potential of −1V using Ag/AgCl electrodes is placed on the sample side, while the outlet is placed at earth ground. A sampling frequency of 100 KHz is set and the Axopatch 200 B is used to apply the DC bias, and data is recorded using Clampfit 10.6.

In some experiments, approximately 5 μl of sample was placed in the inlet microchannel. The outlets were filled with 1×PBS. The outlets were also connected using a T-shaped connector that led to a vacuum pump used for withdrawal. A syringe pump was used to inject sample at a specified flow rate to one end of the inlets, while a small drop of solution was placed at the other inlet. The current trace recordings from the nCC were carried out with a custom made current amplifier, which consisted of a transimpedance amplifier (TIA) that was battery powered with a gain of 100 nA/V and a single-pole-3 db and a bandwidth of 10 kHz. The output of the TIA was digitized by a National Instruments model NI PXIe-6341 DAQ system at a sample rate of 250 kbps by running WinEDR software (Strathclyde Electrophysiology Software).

COMSOL Simulations

The nCC design was built in AutoCAD and imported into COMSOL v5.5. The physics used was Electric currents to model the potential, field strength, and current density across the nanopores. Laminar flow in the microfluidic chip was used to estimate the velocity and pressure. The buffer used was 1×PBS. The inlet/outlet conditions vary through different iterations; atmospheric pressure (1 atm) was set at the inlet and a 3 μL/min was used. The outlet was set to 97000 Pa in some experiments and 50000 Pa for other experiments, but can range therebetween. The simulation was run in a stationary mode and the results were evaluated. Line plots were used to determine the velocity, pressure, potential, electric field strength, and the current density profiles. The effective pore length was calculated from the current density at the full width half-maximum.

Simulations aimed to gauge the feasibility (SNR) for enumerating 30-150 nm particles within 50-200 nm nanopores were carried out. Detectable current transient events were generated for all particles if nanopores were appropriately sized, and current spikes scaled cubically with particle size (FIGS. 4D-4E). Recorded peak amplitudes and widths can be used to determine the transit time of the particles within the sensing element. The pore size (~224 nm effective diameter) was predicated on optimizing the amplitude of the RPS signal with respect to the SARS-CoV-2 particle size as determined using nanoparticle tracking analysis (NTA), which indicated an average particle diameter of ~143 nm. The line graph of the voltage shows that the majority of the potential drops across the nanochannel and nanopore with a sharp drop of 0.04 V across the pore, when a 1V DC bias was applied across the fluidic circuit (FIG. 4D). The corresponding field strength graph shows a higher field strength at the nanopore due to its smaller dimensions with respect to the nanochannel and microchannels. However, the field strength extended out from the physical dimensions of the nanopore, thus increasing the effective length of the nanopore from 100 nm to 224 nm (FIG. 4E).

Figure 9H:
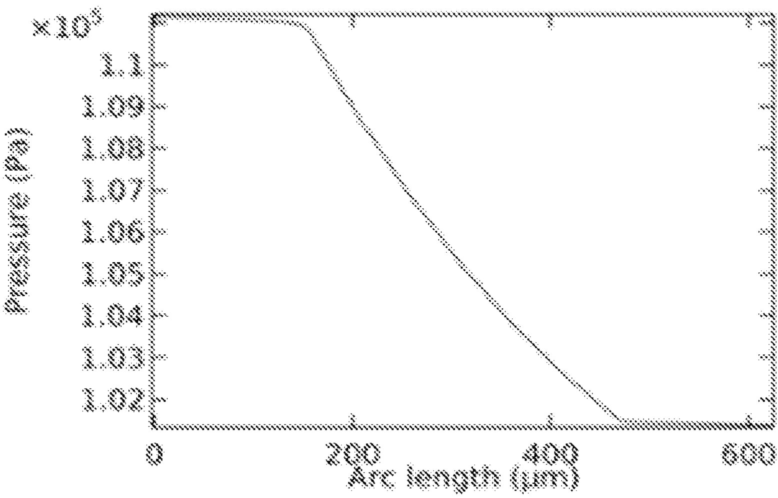
FIG. 9H includes a graph that illustrates pressure versus Arc length of the field of the pore of FIGS. 9A-9C.
Figure 9I:
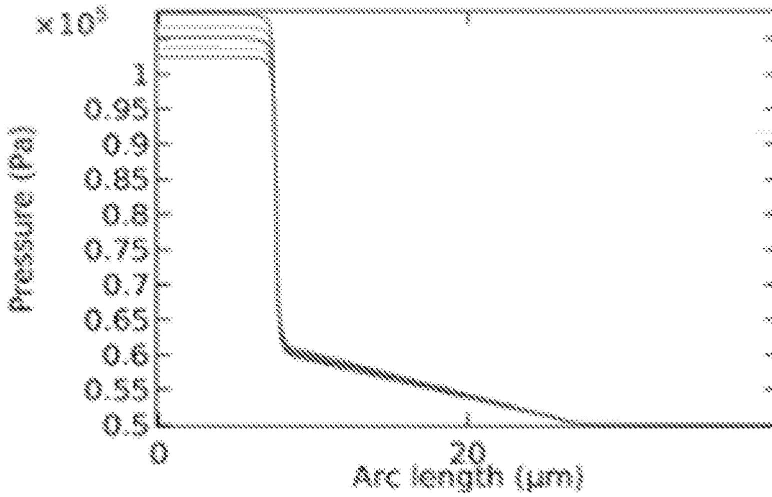
FIG. 9I includes a graph that illustrates pressure versus Arc length of the pore of FIGS. 9A-9C.

The nanochannel 800 having the nanopore 802 were studied with COMSOL simulations. A combination of electrokinetic and hydrodynamic flow was used for fluidic operation for the nCC having five nanochannels 800. Hydrodynamic flow was used to bring particles to the nCC sampling region, which was defined as the 10 μm wide microchannel adjacent to the in-plane pores, and vacuum pressure pulling particles through the pores. COMSOL simulations were performed on the optimized nCC design having pores of 350 nm×100 nm (w×l; design dimensions produced via FIB milling) with conditions at the inlet having a 1 μL/min volume flow rate for delivering particles to the sampling region of the device. The outlet vacuum channel was held at 50 kPa (0.5 atm). The particle velocity in the microchannel ranged from 0.1 m/s in the wider part of the microchannel (near the inlets) and increased to 0.25 m/s in the sampling region, which was placed in front of the in-plane pores. The velocity through the five in-plane pores indicated that they were uniform reaching a velocity of 1.5 m/s, which would give a pulse duration of 0.45 μs. The pressure profile (FIGS. 9H-9I) showed a drop in pressure between the sampling microchannel and the outlet microchannel in FIG. 9H. FIG. 9H shows the pressure drop across the inlet microchannel. The inlet microchannel had a 1 μL/min inflow rate, which drove the particles from the inlet microchannel to the sampling zone and was 10 μm (width) in the sampling region adjacent to the five in-plane pores. However, the majority of the pressure drop (~40 kPa) occurred across the in-plane pores with ~10 kPa pressure drop in the connecting channel following the pores as shown in FIG. 9I. The velocity profile with the inlets set to atmospheric pressure on one side of the inlet and the other side set to operate at a volumetric flow rate of 1 μL/min. The outlets were set to a pressure 50,000 Pa (estimated from the pressure sensor). The pressure drop in the inlet microchannel showing a small pressure drop of 3500 Pa. The particle velocity in the microchannel ranged from 0.1 m/s in the wider part of the microchannel (near the inlets) and increased to 0.25 m/s in the sampling region. The velocity through the five in-plane pores indicated that they were uniform reaching a velocity of 1.5 m/s.

Scanning Electron Microscopy (SEM)

SEMs of the thermoplastic microfluidic/nanofluidic devices and PUA resin stamps were acquired using a Hitachi FlexSEM 1000 II SEM (Hitachi). The thermoplastics were sputter coated with a 10 nm conductive Au layer prior to SEM using a Denton Desk II Sputter Coater. SEM images of the Si mold master was acquired using a Quanta™ 3D DualBeam™ FEG FIB-SEM (FEI). The SEM images are shown in the figures.

Nanoparticle Tracking Analysis (NTA)

Particles were analyzed via NTA (Nanosight NT 2.3). The SARS stock samples were diluted 30× and vortexed prior to analysis. The instrument parameters used for the analysis consisted of: (i) Camera shutter 1206; (ii) camera gain 366; and (iii) capture duration 90 s. Five videos were taken for each sample at 25° C. The flow cell of the Nanosight instrument was washed 5 times with PBS in between sample analyses. During the final wash with PBS, a video was monitored to check if there were any particles left in the flow cell. If particles were detected, washing was continued until no particles were seen.

Figure 12A:
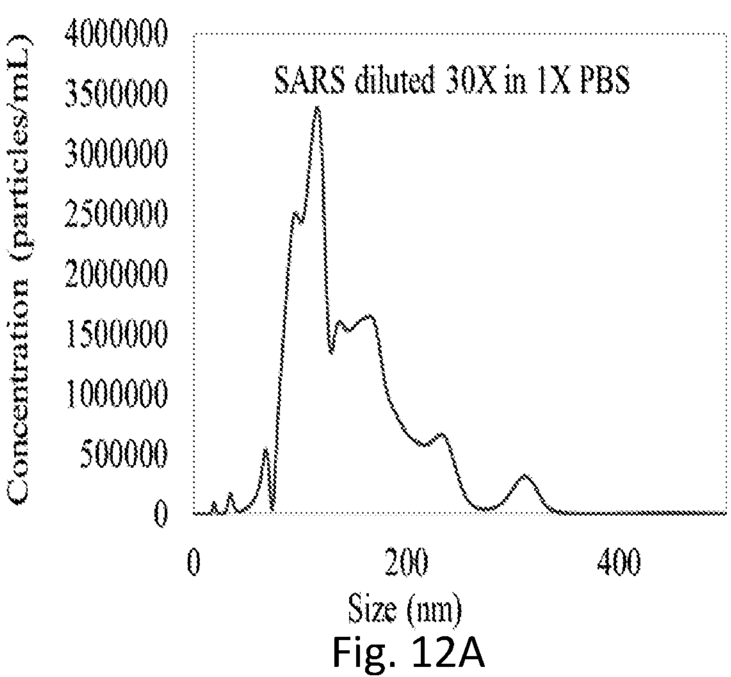
FIG. 12A includes a graph that illustrates the concentration of particles versus size.

The SARS CoV-2 particle was used in nCC detection using a forward flow rate of 1 μL/min and a vacuum pump simultaneously withdrawing fluid to evaluate the performance of the nCC possessing a 350 nm effective diameter and five in-plane pores placed in parallel. In these experiments, heat-inactivated SARS-CoV-2 particles were seeded into 1×PBS (pH=7.4), which was selected to keep the virions close to physiological conditions to prevent any deleterious effects arising from the use of high salt concentrations that may induce virion damage. FIG. 12A shows a nanoparticle tracking analysis (NTA) of the viral particles with a mean particle size of 143.7±5 nm and all particles having sizes <350 nm, which accommodates the selected in-plane pore size to reduce failure due to particle blocking of the in-plane pores.

Figure 12B:
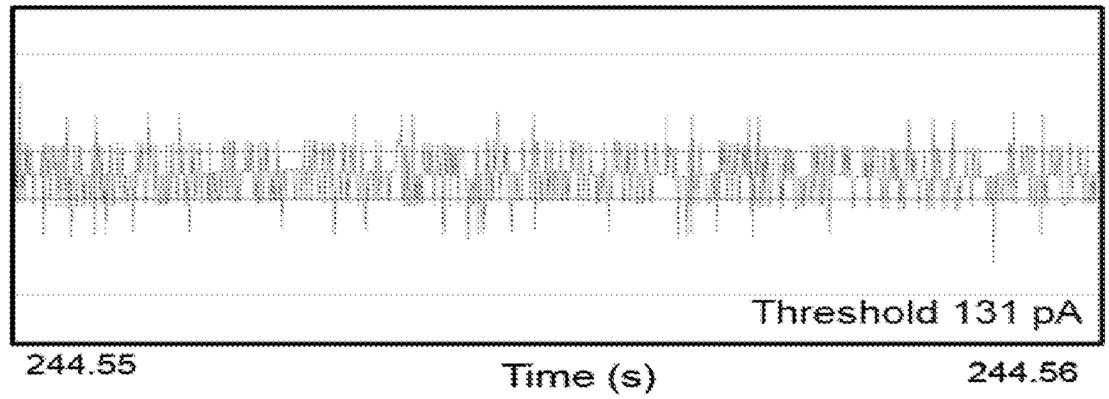
FIG. 12B includes a graph of a data trace for the nCC having the five nanochannels with nanopores in accordance with the pore of FIG. 9.

The average width of the current transient events at half-height and the average event amplitudes at applied voltages of 1 and 5 V were determined. For these measurements, the current transients were measured using an in-house built current transient amplifier (TIA) with the nCC containing Ag/AgCl electrodes for recording electrical signals at the appropriate applied voltage. FIG. 12B shows an expanded region of the data (0.01 s); applied voltage=1 V. The sampling frequency was 100 kHz, and the data was subjected to a high pass filter of 400 Hz, a low pass filter set at 10 kHz, and the baseline was adjusted to a 0 nA current level. An event was scored only if it had >1 data point per peak, an amplitude greater than the threshold, and a half-width ≥0.02 ms. As can be seen, the 1×PBS buffer resulted in no events exceeding the threshold condition.

Figure 12C:
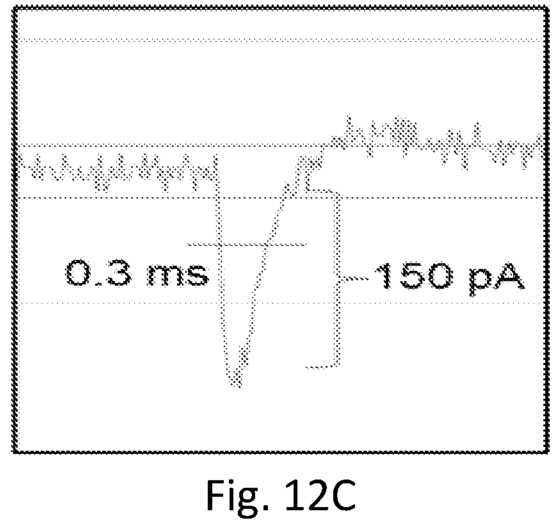
FIG. 12C includes a graph of a data trace for a particle detection event.
Figure 12D:
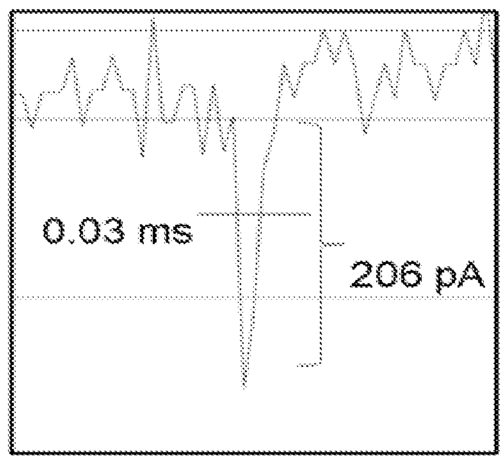
FIG. 12D includes a graph of a data trace for another particle detection event.

We next seeded 52,000 SARS-CoV-2 particles/mL into the 1×PBS buffer and searched for events elicited by the nCC for a 300 s counting interval and an applied voltage of 1 V and 5 V. A threshold level was set with respect to the open pore current to reduce the false positive rate to 0 over the 300 s counting interval. Events having both positive and negative polarity were observed for both applied voltages. Expanded time-scale traces are shown in FIG. 12C for a negative event having an amplitude of 150 pA with a half-width of 0.3 ms (1 V); and FIG. 12D shows a negative event having an amplitude of 206 pA with a half-width of 0.03 ms (5 V). A positive pulse arises from the local modulation of the ionic concentration, where the surface charge of the particle adds to the existing ionic concentration and causes a momentary increase in the in-plane pore conductance.[46,47] Moreover, particles could be porous causing it to become more conductive than the carrier electrolyte, which in this case was 1×PBS with an ionic concentration of ~162.7 mM. In the case of negative polarity peaks, a volume exclusion process induced a lower pore conductance compared to the open pore. The occurrence of both positive and negative polarity events in our RPS trace data indicates disparity in particle surface charge and possibly porosity of the enveloped particle.

The peak amplitude histogram (FIG. 12E) showed an average amplitude of 146 pA ($V_{bias}$=1 V). The event width (FWHM) or dwell time ranged from 0.03 ms to 1.1 ms (FIG. 12F) with an average half width found to be 0.34 ms and an average width of events at the base of 1.27 ms indicating the sampling frequency is sufficient (34 data points for a 0.34 ms half-width and 127 data points for a 1.27 ms event) to minimize signal aliasing. However, with the bandwidth of the electronics set to 10 kHz, some perturbation in peak shape with a FWHM <0.1 ms could occur.

Because SARS CoV-2 particles have a negative zeta potential, the applied voltage was increased from 1 V to 5 V to potentially increase sampling efficiency. The average peak amplitude at 5 V was estimated to be 295 pA (FIG. 12G) with an average FWHM of 0.04 ms (FIG. 12H). Compared to the 1 V data, there was a reduction in the average FWHM of events from 0.34 ms to 0.04 ms. This was attributed to the higher bias voltage, which induced a higher electrophoretic force that caused the particles (negatively charged) to translocate faster through the in-plane pores of the nCC. However, the current transient amplitude increased from 146 pA to 295 pA, an approximate 100% increase in the average event amplitude. In addition, we found that the event frequency increased from 72 to 123 events with a bias voltage increase from 1 V to 5V over the same counting interval (300 s) and SARS-CoV-2 particle concentration.

Figure 12E:
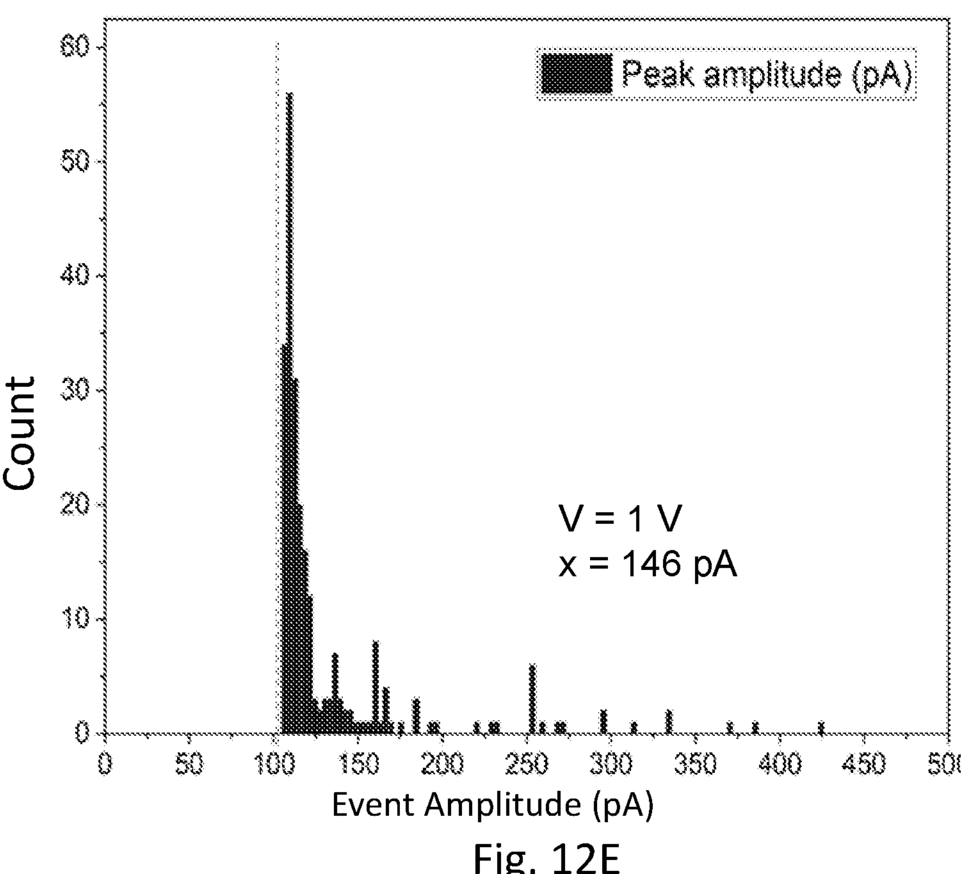
FIG. 12E includes a graph that shows the counts per event amplitude.
Figure 12F:
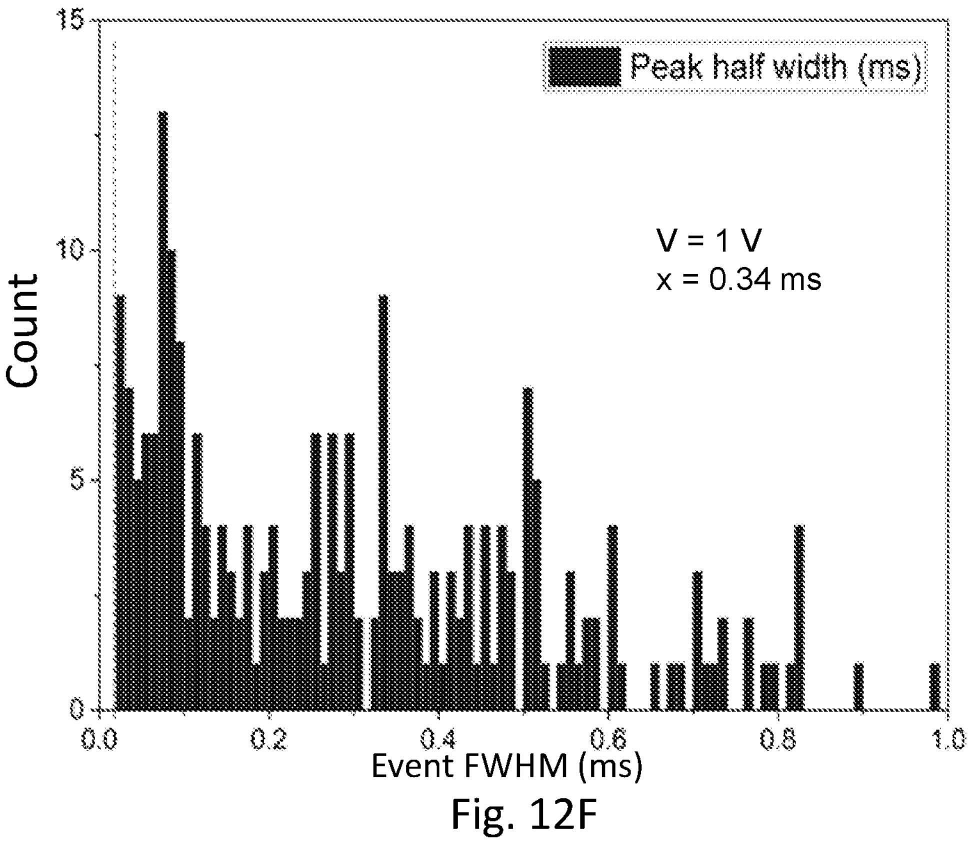
FIG. 12F includes a graph that shows the counts per event FWHM.
Figure 12G:
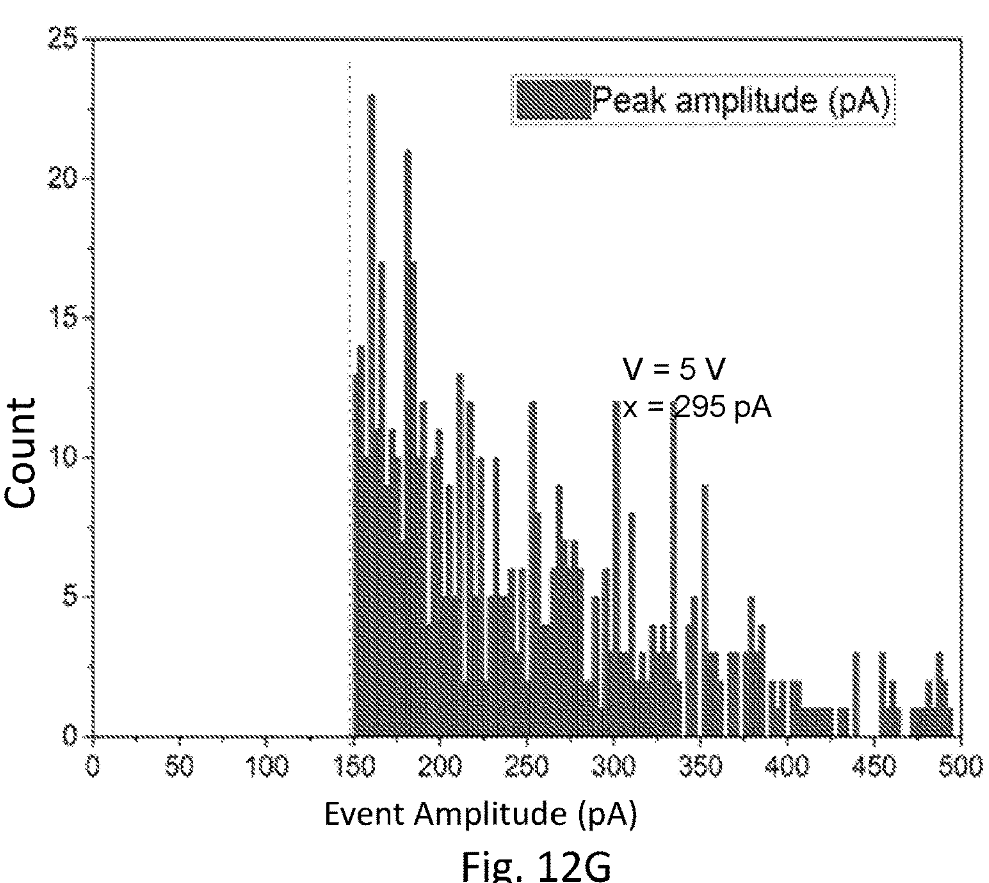
FIG. 12G includes a graph that shows the counts per event amplitude.
Figure 12H:
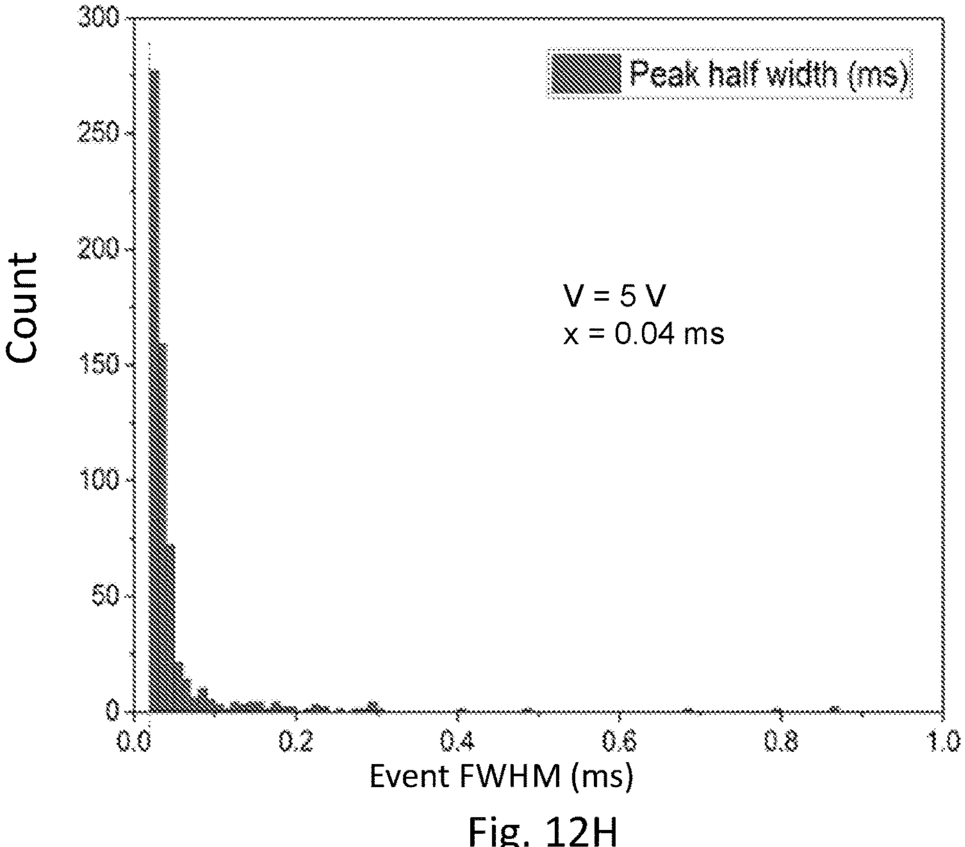
FIG. 12H includes a graph that shows the counts per event FWHM.

FIG. 12E shows the histogram showing the distribution of peak amplitudes with an average peak amplitude of 146 pA at 1 V. FIG. 12F shows the dwell time half width distribution of events for a bias voltage of 1 V with and an average half-width of 0.34 ms. FIG. 12G shows the histogram showing the distribution of peak amplitudes with an average peak amplitude of 295 pA using an applied voltage of 5 V. FIG. 12H shows the dwell time half width distribution of events with an average half-width of 0.04 ms for an applied voltage of 5 V.

A calibration curve (not shown) was built from the average number of events observed over a defined counting interval (300 s) and an applied voltage of 5 V. A linear correlation was obtained ($R^2$=0.9976). The concentration LOD was estimated to be $2.4\times10^3$ particles/mL with a sampling efficiency of $1.6\times10^{-2}$% and a lower limit-of-quantification (LOQ) of $8.10\times10^3$ particles/mL. The concentration LOD improved from $6\times10^6$ particles/mL using the single pore device to $2.4\times10^3$ particles/mL in the device reported herein due to increases in the sampling efficiency arising from the use of multiple pores in parallel, the reduction in size of the sampling microchannel, increases in the vacuum withdrawal pressure drop, optimal forward flow input rate, and placement of the pores next to the sampling microchannel with the tapered funnel interface. Overall, there was a 2,400-fold improvement in the concentration LOD with our optimized design compared to the single pore device.[40]

Calibration Curve for Viral Particle Counting

SARS CoV-2 particles that were pre-heat inactivated were purchased from ATCC having a stock concentration of $4\times10^8$ particles/ml. Two different calibration curves were performed: In case of a single nanochannel with a nanopore, the samples for the calibration curve were prepared by serially diluting the stock in 1×PBS with concentrations ranging from $10^6$ to $10^8$. About 5 µl of the prepared samples were filled into the inlet reservoir side of the nCC chip's microchannel. The buffer side was filled with 1×PBS and a syringe pump was connected to the buffer side set to withdrawal at 20 µl/min. The sample and the buffer sides were electrically connected by placing Ag/AgCl electrodes into them to establish ohmic contact and a DC bias of −1 V was applied. Data was recorded using an Axopatch 200B with the data analyzed using Clampfit 10.1. Three sets of data were collected.

In the case of the five nanochannels and nanopores, the dilutions from the stock solution of SARS-CoV-2 were serially diluted to establish clinically relevant concentrations with the concentrations verified using NTA[45] (the seeding levels varied between $1\times10^3$ copies/mL and $1\times10^6$ copies/mL to represent VP load in clinical samples). About 5 µl of the samples were used to fill one reservoir of the input microchannel while the outlet was filled with 1×PBS. A forward flow of sample was used to inject sample into the device at 3 µl/min and directed from the inlet reservoir and to the outlet reservoir with the outlet channel set to vacuum withdrawal. The TIA was used to apply a voltage of −5 V using Ag/AgCl electrodes and the entire set up was placed in a custom made Faraday cage. A minimum of 3 sets of data were collected.

A calibration curve based on clinically relevant concentrations can be built to correlate the number of events observed to the concentration of the viral load, which gave us a limit of detection (LOD) of 2,500 particles/mL. This will help determine the viral load in clinical samples, thus proving its capability as a preliminary diagnostic tool to diagnose COVID-19.

Pressure Sensing at the Withdrawal End

The withdrawal rate was determined by a pressure drop across the in-plane pores obtained using a flow rate of 20 µl/min. The vacuum withdrawal was estimated by connecting the outlet reservoirs to a T-shaped connector with a pressure sensor connected to it. One end of the pressure sensor was connected to a multimeter from which readings were recorded, while the other end extended into the withdrawal system. The withdrawal was turned on and the reading from the pressure sensor connected to a multimeter was recorded for a period of 720 s. The data was registered in terms of mV, which was then converted into pressure. The drop in pressure with respect to the atmospheric pressure was noted.

Fluorescence Measurements

Rhodamine-B (Ex/Em: 534/570) was used as a tracer to check if the devices were sealed well. About 5 µL of 100 nM dye was used to fill the inlet and the dye was tracked as it passed through the nCC using a 532 nm Nd:YAG laser equipped with a 100× oil immersion objective (NA: 1.4). Nile red beads (Ex/Em 552/636) of 40 nm and 100 nm were diluted to 107 particles/mL in 1 M NaCl and 1×PBS, which was filled at the inlet side of the nano-Coulter Counter device's fluidic network. The outlet end was connected to a syringe pump withdrawing liquid at 20 µL/min. The single-molecule fluorescence microscope was equipped with a 60×/100× objective and was used to track the particles moving through the nCC. The microscope system was fitted with a sCMOS camera that recorded the data in Metamorph software at an exposure of 10 ms, a binning of 1×1, and analysed using Fiji.

Forward Flow Rates

It can be helpful to have a continuous supply of particles within the sampling region of the nCC device. Therefore, a SARS CoV-2 particle suspension ($2.6\times10^6$ particles/mL) was processed through the nCC chip at various volume flow rates. A potential of 1 V was applied at the outlet end of the sampling region and the vacuum outputs were grounded with the vacuum pump set at 0.5 atm. The inlet flow rate ranged from 0.1 µL/min to 10 µL/min and the number of events detected for each volume flow rate was measured. It was found that the number of events at 1 µL/min was higher compared to other flow rates. The reason for these results could be due to the fact that at a volume flow rate <1 µL/min there are not sufficient number of particles brought into the sampling region for the 300 s counting interval and at flow rates >1 µL/min, fewer particles have the opportunity to be drawn into the pores hydrodynamically and/or electrokinetically.

COVID-19 Detection

We collected 10 saliva samples through an IRB approved protocol at the University of Kansas Medical Center. Of the 10 samples, 5 were COVID-19 negative as determined via RT-qPCR and 5 were COVID-19 positive. Because the sample input was saliva, before doing the nCC enumeration we specifically enriched the SARS-CoV-2 particles using an affinity-enrichment microfluidic chip, which consisted of a pillared chip containing ~1.5M pillars; (10 µm×10 µm, 10 µm spacing) positioned in 7-parallel beds to allow for high throughput processing. This chip was made from COP via injection molding to allow for high-scale production.[52] The high number of pillars (i.e., high surface area) along with the small inter-pillar spacing (i.e., reduced diffusional distances) allowed for a high dynamic range and recovery, respectively, of viral particles.[48]

We employed a DNA aptamer as the affinity agent ($K_d$=5.8 nM)[49] targeting the ACE2 receptor binding domain (RBD) of the Spike protein of SARS-CoV-2. The aptamer contained a 3' inverted dT (deoxy-thymidine) residue[50] to increase its stability in the presence of 3' exonucleases and a 5' amino-linker and PEGylation that can extend the half-life in biological samples as well as provide attachment to surface carboxylic acid groups.[51] For the covalent attachment of the aptamer to the selection chip's surface, we used a photocleavable (PC) 7-amino coumarin heterobifunctional linker.[52] The use of this photocleavable linker allowed for the specific surface capture/enrichment of the virus particles and then, blue light release from the surface intact viral particles to allow for their enumeration via the nCC. The recovery of native SARS-CoV-2 µsing the 51 nt aptamer and selection chip has been found to be 94.7±7% and can distinguish between active and non-active SARS-CoV-2 virions.[53]

The COVID-19(−) saliva samples generated no discernable signals in the nCC RPS data traces. This resulted from the high specificity afforded by the selection chip and its affinity agent; our previous report on the specificity of the selection chip using the 51 nt aptamer for the human respiratory syncytial virus (HRSV), human Alphacoronavirus 229E (HCoV 229E), and Betacoronavirus 1 (HCoV OC43) indicated minimal to no recovery based on RT-qPCR results when using the SARS-CoV-2 aptamer.

Saliva samples that were COVID-19(+) were analyzed as well using the selection chip with photo-release followed by nCC enumeration. Based on sequencing data (gisaid.org/phylodynamics/global/nextstrain),[54] the most frequently detected SARS-CoV-2 clade in KS and MO in Summer 2021 was the Delta variant. The Delta variant has mutations in the RBD region, which were K417N, L452R, and T478K that have been shown to increase affinity binding to ACE2 receptors.[55] While these mutations can effect epitope orientation causing immune escape from large antibodies (150 kDa), smaller molecules such as aptamers (≤16 kDa) may be less affected by epitope orientation.[56] As can be seen from the data shown in Table 1, the system successfully identified all five COVID-19(+) samples using the affinity selection chip and the nCC. In our previous report using a single-pore nCC device, which was also made from COP but fabricated via nanoimprint lithography (NIL), spike-in samples of SARS-CoV-2 into saliva (concentration=~$10^8$ particles/mL) showed a poorer concentration LOD (5.8×$10^6$ particles/mL),[40] which would not cover the entire dynamic range of viral particles typically found in COVID-19 patients ($10^2$-$10^8$ particles/mL[57]). However, the 5-pore nCC design with optimized operation parameters can cover this range.

Table 1 Shows the Variant Delta Lineage B.1.617.2 Jul. 2021-Dominant variant at time of testing

| COVID-19+ | Counting time interval (sec) | Height (pA) | Half-Width (ms) |
|---|---|---|---|
| 6 | 100 | 360 +/− 584 | 0.027 +/− 0.01 |
| 7 | 100 | 217 +/− 136 | 0.045 +/− 0.078 |
| 8 | 100 | 380 +/− 197 | 0.029 +/− 0.018 |
| 9 | 100 | 243 +/− 122 | 0.069 +/− 0.0001 |
| 100 | 100 | 316 +/− 103 | 0.04 +/− 0.01 |

High Grade Serous Ovarian Cancer (HGSOC) EV Detection

Figure 13A:
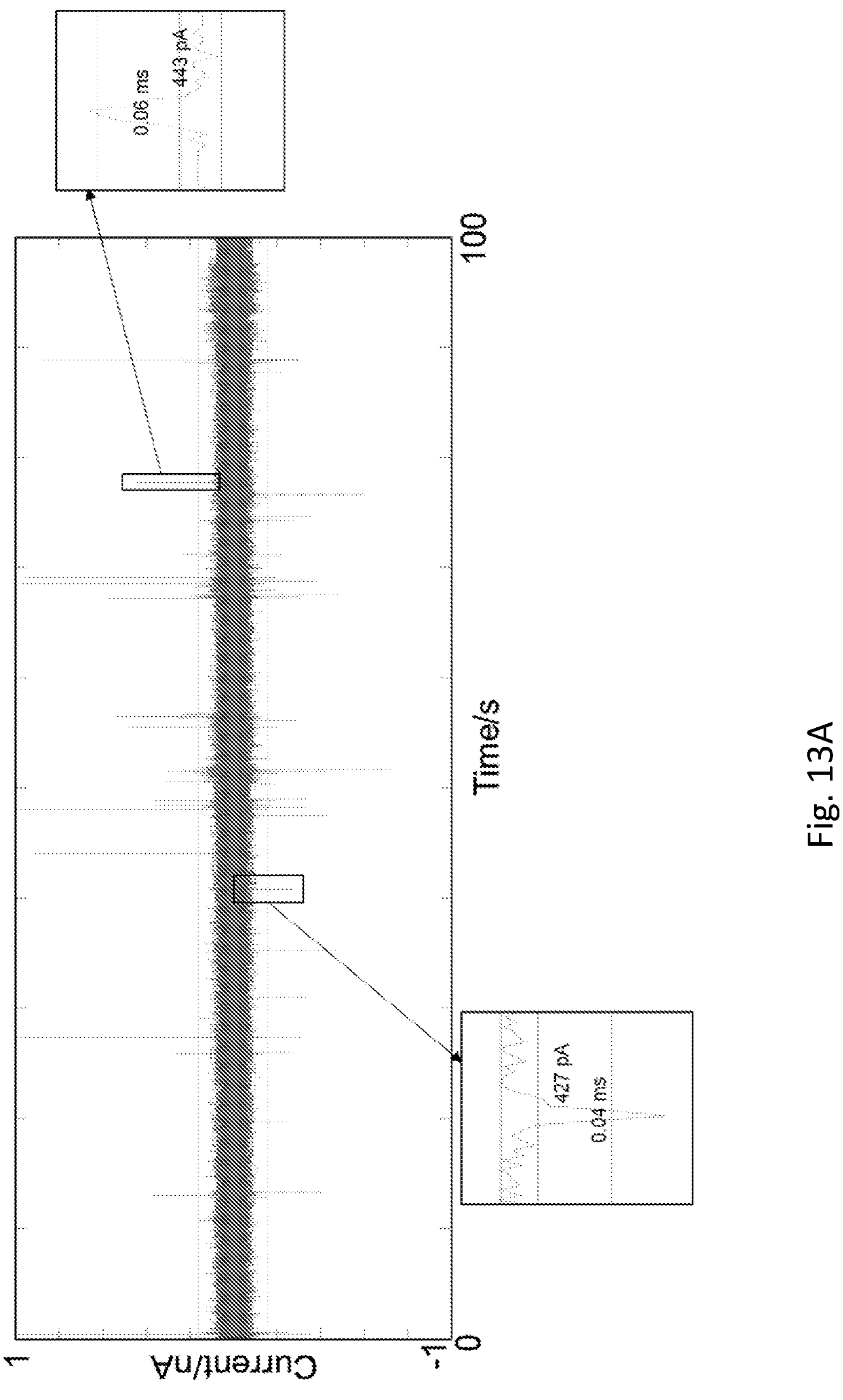
FIG. 13A includes a graph of a data trace for a particle detection events, with two particle detection events being magnified along the time scale.

To evaluate the feasibility of using the selection and nCC chips for sampling EVs from plasma samples, 6 de-identified high-grade serous ovarian cancer patients and 6 healthy donors were analyzed using an anti-MUC16 monoclonal antibody, which recognizes specifically the glycosylated MUC-16 protein that is EV-membrane bound, modified selection chip and following capture, the recovered particles were photo-released into a volume of ~35 μL with 1×PBS. A typical RPS trace of EVs selected from a HGSOC patient's plasma is shown in FIG. 13A. As can be seen, both negative and positive polarity events were detected as we noted for SARS-CoV-2. Data indicated highly monodispersed particles with an average size of ~133 nm as determined by NTA (see FIG. 13B).

Figure 13B:
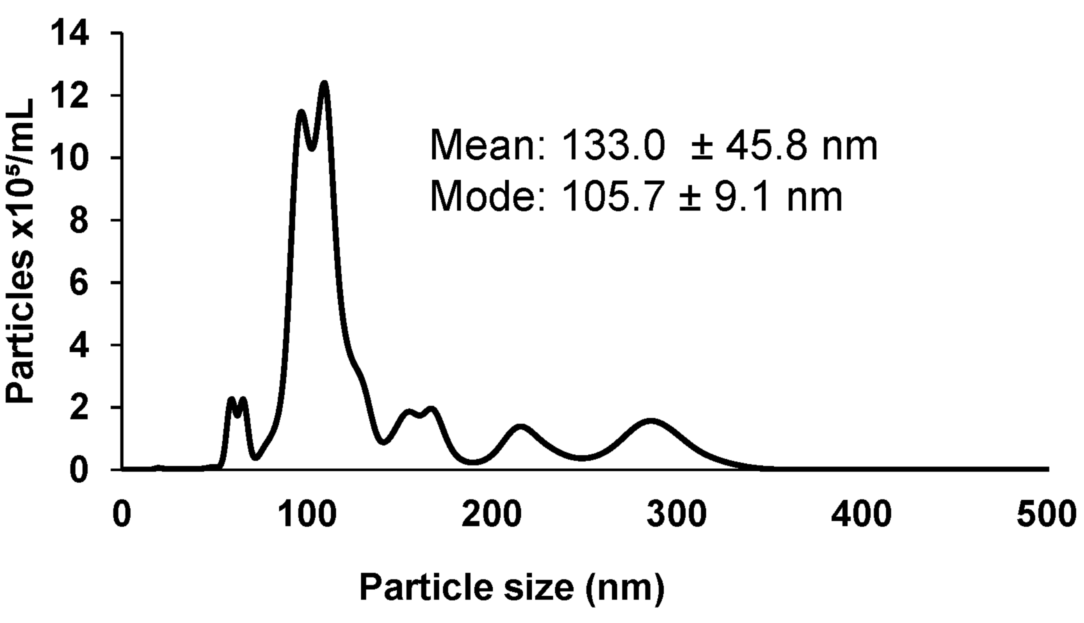
FIG. 13B includes a graph of the particle size distribution.
Figure 13C:
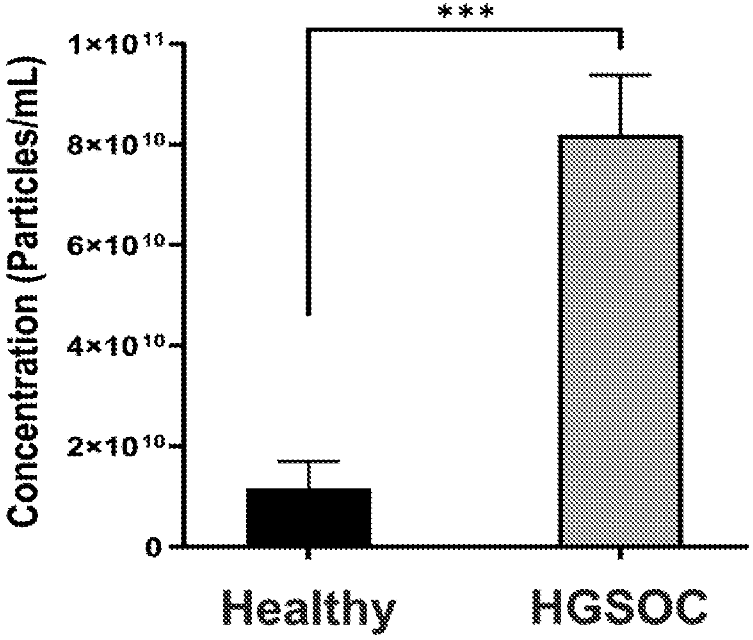
FIG. 13C includes a graph that shows the concentration of particles for healthy patients versus the patients that have cancer.

As can be seen from FIG. 13C, a group of samples had a much higher selected EV concentration with a range from 7.46×$10^{10}$ particles/mL to 9.56×$10^{10}$ particles/mL, compared to another group, which had a mean particle frequency of 1.77×$10^{10}$ particles/mL. The samples were placed into one of two groups and labeled as HGSOC vs. healthy donors based on the number of EVs detected using the nCC. The two groups showed a significant difference with a p-value of 0.0007; the higher concentration group was assigned to those with HGSOC. Patient annotation data for these samples indicated that the groups assigned to each sample concurred with the clinical designation (clinical sensitivity and specificity=100% for this proof-of-concept clinical study).

FIG. 13A shows a RPS trace from the nCC device having five parallel pores made in COP via injection molding. The EVs were affinity selected using anti-MUC16 mAbs poised within the selection chip. Following enrichment, the selected particles were released from the chip's surfaces and sent to the nCC for enumeration. The measurement was performed in 1×PBS with an applied voltage of −5 V. Also shown are single peak traces with amplitudes >400 pA and half-widths or ~0.05 ms (positive and negative polarity peaks are shown). FIG. 13B shows the NTA analysis of MUC16 expressing EVs that were selected and released from the selection chip. As seen, the average particle size was 133 nm. FIG. 13C shows the abundance of MUC16 expressing EVs from the plasma of healthy donors and patients with high grade serous ovarian cancer (HGSOC).

5 Pores in Parallel

The rationale behind choosing 5 pores was to improve the sampling efficiency by providing more area for the particles to be sampled from the access microchannels while being able to preserve the signal to noise ratio of single particles. The final design had a pore of 350 nm (width) and hence the calculations were based on this dimension. There are two ways to achieve this; 1) Having a single pore of 1.75 μm wide or 2) fabricating 5 pores in parallel with each pore having a width of 350 nm.

From our experiments, the current at 1 V potential across the 5 pores in parallel is 14 nA;

$$V = IR$$

$$R = \frac{V}{I} = \frac{1\text{ V}}{14}\text{nA} = 71.4\ \text{M}\Omega \text{ (For a single 350 nm pore)}$$

$$\frac{1}{R_T} = \frac{1}{R} + \frac{1}{R} + \frac{1}{R} + \frac{1}{R} + \frac{1}{R} = \frac{5}{R}$$

$$R_T = \frac{R}{5} \quad R = 5R_T$$

$$R = 357.1\ \text{M}\Omega \text{ (Total for a single 1.7 }\mu\text{m pore)}$$

R=357.1 MΩ (Total for a single 1.75 μm pore)

Case 1: Single 1.75 μm pore $$R_T = 357.1\ \text{M}\Omega$$

$$I = 14\text{ nA} \times 5 = 70\text{ nA}$$

$$\text{Pore diameter} = 1750\text{ nm; Assume virus diameter} = 150\text{ nm;}$$

Pore diameter=1750 nm; Assume virus diameter=150 nm;

$$\text{Occlusion Ratio} = (150\text{ nm}/1750\text{ nm}) \times 100\% = 8.6\%$$

$$\Delta I = (8.6/100) \times 70\text{ nA} = 6.02\text{ nA in 70 nA}$$

Case 2:5 Pores in Parallel

R=71.4 MΩ (Single 350 nm pore)

Pore diameter=350 nm; Assume virus diameter=150 nm;

$$R = 71.4\ \text{M}\Omega \text{ (Single 350 nm pore)}$$

$$\text{Pore diameter} = 350\text{ nm; Assume virus diameter} = 150\text{ nm;}$$

$$\text{Occlusion Ratio} = (150\text{ nm}/350\text{ nm}) \times 100\% = 42.86\%$$

$$I_T = 14\text{ nA} \times 5 = 70\text{ nA}$$

$$\Delta I = (42.86/100) \times 14\text{ nA} = 6.02\text{ nA in 70 nA}$$

Electronically, both methods yielded the same result, which was evident from the ΔI calculation. However, we estimated the effective length by calculating the FWHM from the current density plot from COMSOL simulations.[54] This was designed to have a pore width of 1.75 μm and a length of 100 nm. The connecting nanochannels were designed to have a width 4 μm having a total length of 20 μm between the microchannels. A potential of −5 V was applied to the inlet microchannel and the outlet was placed at earth ground.

One skilled in the art will appreciate that, for the processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In one embodiment, the present methods can include aspects performed on a computing system. As such, the computing system can include a memory device that has the computer-executable instructions for performing the methods. The computer-executable instructions can be part of a computer program product that includes one or more algorithms for performing any of the methods of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor.

There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive (HDD), a compact disc (CD), a digital versatile disc (DVD), a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communication link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems, including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. Such depicted architectures are merely exemplary, and that in fact, many other architectures can be implemented, which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

FIG. 10 shows an example computing device 1000 (e.g., a computer) that may be arranged in some embodiments to perform the methods (or portions thereof) described herein. In a very basic configuration 1002, computing device 1000 generally includes one or more processors 1004 and a system memory 1006. A memory bus 1008 may be used for communicating between processor 1004 and system memory 1006.

Depending on the desired configuration, processor 1004 may be of any type including, but not limited to: a microprocessor (μP), a microcontroller (μC), a digital signal processor (DSP), or any combination thereof. Processor 1004 may include one or more levels of caching, such as a level one cache 1010 and a level two cache 1012, a processor core 1014, and registers 1016. An example processor core 1014 may include an arithmetic logic unit (ALU), a floating point unit (FPU), a digital signal processing core (DSP Core), or any combination thereof. An example memory controller 1018 may also be used with processor 1004, or in some implementations, memory controller 1018 may be an internal part of processor 1004.

Depending on the desired configuration, system memory 1006 may be of any type including, but not limited to: volatile memory (such as RAM), non-volatile memory (such as ROM, flash memory, etc.), or any combination thereof. System memory 1006 may include an operating system 1020, one or more applications 1022, and program data 1024. Application 1022 may include a determination application 1026 that is arranged to perform the operations as described herein, including those described with respect to methods described herein. The determination application 1026 can obtain data, such as pressure, flow rate, and/or temperature, and then determine a change to the system to change the pressure, flow rate, and/or temperature.

Computing device 1000 may have additional features or functionality, and additional interfaces to facilitate communications between basic configuration 1002 and any required devices and interfaces. For example, a bus/interface controller 1030 may be used to facilitate communications between basic configuration 1002 and one or more data storage devices 1032 via a storage interface bus 1034. Data storage devices 1032 may be removable storage devices 1036, non-removable storage devices 1038, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and non-volatile, removable and non-removable media implemented in any method or technology for storage of information, such as computer readable instructions, data structures, program modules, or other data.

System memory 1006, removable storage devices 1036 and non-removable storage devices 1038 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 1000. Any such computer storage media may be part of computing device 1000.

Computing device 1000 may also include an interface bus 1040 for facilitating communication from various interface devices (e.g., output devices 1042, peripheral interfaces 1044, and communication devices 1046) to basic configuration 1002 via bus/interface controller 1030. Example output devices 1042 include a graphics processing unit 1048 and an audio processing unit 1050, which may be configured to communicate to various external devices such as a display or speakers via one or more A/V ports 1052. Example peripheral interfaces 1044 include a serial interface controller 1054 or a parallel interface controller 10, which may be configured to communicate with external devices such as input devices (e.g., keyboard, mouse, pen, voice input device, touch input device, etc.) or other peripheral devices (e.g., printer, scanner, etc.) via one or more I/O ports 1058. An example communication device 1046 includes a network controller 1060, which may be arranged to facilitate communications with one or more other computing devices 1062 over a network communication link via one or more communication ports 1064.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 1000 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 1000 may also be implemented as a personal computer including both laptop computer and non-laptop computer configurations. The computing device 1000 can also be any type of network computing device. The computing device 1000 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In some embodiments, a computer program product can include a non-transient, tangible memory device having computer-executable instructions that when executed by a processor, cause performance of a method that can include: providing a dataset having object data for an object and condition data for a condition; processing the object data of the dataset to obtain latent object data and latent object-condition data with an object encoder; processing the condition data of the dataset to obtain latent condition data and latent condition-object data with a condition encoder; processing the latent object data and the latent object-condition data to obtain generated object data with an object decoder; processing the latent condition data and latent condition-object data to obtain generated condition data with a condition decoder; comparing the latent object-condition data to the latent-condition data to determine a difference; processing the latent object data and latent condition data and one of the latent object-condition data or latent condition-object data with a discriminator to obtain a discriminator value; selecting a selected object from the generated object data based on the generated object data, generated condition data, and the difference between the latent object-condition data and latent condition-object data; and providing the selected object in a report with a recommendation for validation of a physical form of the object. The non-transient, tangible memory device may also have other executable instructions for any of the methods or method steps described herein. Also, the instructions may be instructions to perform a non-computing task, such as synthesis of a molecule and or an experimental protocol for validating the molecule. Other executable instructions may also be provided.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

REFERENCES

1. Coulter, W. H. Means for Counting Particles Suspended in a Fluid. 1949.
2. Shapiro, H. M., The evolution of cytometers. *Cytometry. Part A: the journal of the International Society for Analytical Cytology* 2004, 58 (1), 13-20.
3. Davey, H. M.; Kell, D. B., Flow cytometry and cell sorting of heterogeneous microbial populations: the importance of single-cell analyses. *Microbiological Reviews* 1996, 60 (4), 641-696.
4. Javanmard, M.; Davis, R. W., A microfluidic platform for electrical detection of DNA hybridization. *Sensors and Actuators B: Chemical* 2011, 154 (1), 22-27.
5. Javanmard, M.; Emaminejad, S.; Dutton, R. W.; Davis, R. W., Use of Negative Dielectrophoresis for Selective Elution of Protein-Bound Particles. *Analytical Chemistry* 2012, 84 (3), 1432-1438.
6. Emaminejad, S.; Javanmard, M.; Dutton, R. W.; Davis, R. W., Microfluidic diagnostic tool for the developing world: contactless impedance flow cytometry. *Lab on a Chip* 2012, 12 (21), 4499-4507.
7. Emaminejad, S.; Javanmard, M.; Dutton, R. W.; Davis, R. W., Smart Surface for Elution of Protein-Protein Bound Particles: Nanonewton Dielectrophoretic Forces Using Atomic Layer Deposited Oxides. *Analytical Chemistry* 2012, 84 (24), 10793-10801.
8. Song, Y.; Zhang, J.; Li, D., Microfluidic and Nanofluidic Resistive Pulse Sensing: A Review. *Micromachines* 2017, 8 (7), 204.
9. Traversi, F.; Raillon, C.; Benameur, S. M.; Liu, K.; Khlybov, S.; Tosun, M.; Krasnozhon, D.; Kis, A.; Radenovic, A., Detecting the translocation of DNA through a nanopore using graphene nanoribbons. *Nature Nanotechnology* 2013, 8 (12), 939-945.
10. Rodriguez-Trujillo, R.; Ajine, M. A.; Orzan, A.; Mar, M. D.; Larsen, F.; Clausen, C. H.; Svendsen, W. E., Label-free protein detection using a microfluidic Coulter-counter device. *Sensors and Actuators B: Chemical* 2014, 190, 922-927.
11. Cai, H.; Wang, Y.; Yu, Y.; Mirkin, M. V.; Bhakta, S.; Bishop, G. W.; Joshi, A. A.; Rusling, J. F., Resistive-Pulse Measurements with Nanopipettes: Detection of Vascular Endothelial Growth Factor C (VEGF-C) Using Antibody-Decorated Nanoparticles. *Analytical Chemistry* 2015, 87 (12), 6403-6410.
12. Han, Y.; Wu, H.; Liu, F.; Cheng, G.; Zhe, J., Label-Free Biomarker Assay in a Microresistive Pulse Sensor via Immunoaggregation. *Analytical Chemistry* 2014, 86 (19), 9717-9722.
13. Takakura, T.; Yanagi, I.; Goto, Y.; Ishige, Y.; Kohara, Y., Single-molecule detection of proteins with antigen-antibody interaction using resistive-pulse sensing of submicron latex particles. *Applied Physics Letters* 2016, 108 (12), 123701.
14. Pol, E. V. d.; Coumans, F. A. W.; Grootemaat, A. E.; Gardiner, C.; Sargent, I. L.; Harrison, P.; Sturk, A.; Leeuwen, T. G. v.; Niewuwland, R., Particle size distribution of exosomes and microvesicles determined by transmission electron microscopy, flow cytometry, nanoparticle tracking analysis, and resistive pulse sensing. *Journal of Thrombosis and Haemostasis* 2014, 12, 1182-1192.
15. Vogel, R.; Willmott, G.; Kozak, D.; Roberts, G. S.; Anderson, W.; Groenewegen, L.; Glossop, B.; Barnett, A.; Turner, A.; Trau, M., Quantitative Sizing of Nano/Microparticles with a Tunable Elastomeric Pore Sensor. *Analytical Chemistry* 2011, 83 (9), 3499-3506.
16. Roberts, G. S.; Yu, S.; Zeng, Q.; Chan, L. C. L.; Anderson, W.; Colby, A. H.; Grinstaff, M. W.; Reid, S.; Vogel, R., Tunable pores for measuring concentrations of synthetic and biological nanoparticle dispersions. *Biosensors and Bioelectronics* 2012, 31 (1), 17-25.
17. Fraikin, J.-L.; Teesalu, T.; McKenney, C. M.; Ruoslahti, E.; Cleland, A. N., A high-throughput label-free nanoparticle analyser. *Nature Nanotechnology* 2011, 6 (5), 308-313.
18. Xu, Y., Nanofluidics: A New Arena for Materials Science. *Advanced Materials* 2018, 30, 1702419.
19. Wanunu, M.; Dadosh, T.; Ray, V.; Jin, J.; McReynolds, L.; Drdić, M., Rapid electronic detection of probe-specific microRNAs using thin nanopore sensors. *Nature nanotechnology* 2010, 5 (11), 807-814.
20. Haque, F.; Li, J.; Wu, H.-C.; Liang, X.-J.; Guo, P., Solid-state and biological nanopore for real-time sensing of single chemical and sequencing of DNA. *Nano Today* 2013, 8 (1), 56-74.
21. Ying, Y.-L.; Cao, C.; Long, Y.-T., Single molecule analysis by biological nanopore sensors. *Analyst* 2014, 139 (16), 3826-3835.
22. Davenport, M. W.; Healy, K.; Pevarnik, M.; Teslich, N.; Cabrini, S.; Morrison, A.; Siwy, Z. S.; Létant, S. E., The Role of Pore Geometry in Single Particle Detection. *Biophysical Journal* 2013, 104 (2, Supplement 1), 521a.
23. DeBlois, R. W.; Wesley, R. K., Sizes and concentrations of several type C oncornaviruses and bacteriophage T2 by the resistive-pulse technique. *Journal of virology* 1977, 23 (2), 227-33.
24. Uram, J. D.; Ke, K.; Hunt, A. J.; Mayer, M., Submicrometer Pore-Based Characterization and Quantification of Antibody-Virus Interactions. *Small* 2006, 2 (8-9), 967-972.
25. Zhou, K.; Li, L.; Tan, Z.; Zlotnick, A.; Jacobson, S. C., Characterization of Hepatitis B Virus Capsids by Resistive-Pulse Sensing. *Journal of the American Chemical Society* 2011, 133 (6), 1618-1621.
26. Arjmandi, N.; Van Roy, W.; Lagae, L., Measuring Mass of Nanoparticles and Viruses in Liquids with Nanometer-Scale Pores. *Analytical Chemistry* 2014, 86 (10), 4637-4641.
27. Arjmandi, N.; Van Roy, W.; Lagae, L.; Borghs, G., Measuring the Electric Charge and Zeta Potential of Nanometer-Sized Objects Using Pyramidal-Shaped Nanopores. *Analytical Chemistry* 2012, 84 (20), 8490-8496.
28. McMullen, A.; de Haan, H. W.; Tang, J. X.; Stein, D., Stiff filamentous virus translocations through solid-state nanopores. *Nature Communications* 2014, 5 (1), 4171.
29. Wu, H.; Chen, Y.; Zhou, Q.; Wang, R.; Xia, B.; Ma, D.; Luo, K.; Liu, Q., Translocation of Rigid Rod-Shaped Virus through Various Solid-State Nanopores. *Analytical Chemistry* 2016, 88 (4), 2502-2510.

30. Karawdeniya, B. I.; Bandara, Y. M. N. D. Y.; Khan, A. I.; Chen, W. T.; Vu, H.-A.; Morshed, A.; Suh, J.; Dutta, P.; Kim, M. J., Adeno-Associated Virus Characterization for Cargo Discrimination through Nanopore Responsiveness. *Nanoscale* 2020, 12, 23721-23731.
31. Vogel, R.; Anderson, W.; Eldridge, J.; Glossop, B.; Willmott, G., A Variable Pressure Method for Characterizing Nanoparticle Surface Charge Using Pore Sensors. *Analytical Chemistry* 2012, 84 (7), 3125-3131.
32. Farkas, K.; Pang, L.; Lin, S.; Williamson, W.; Easingwood, R.; Fredericks, R.; Jaffer, M. A.; Varsani, A., A Gel Filtration-Based Method for the Purification of Infectious Rotavirus Particles for Environmental Research Applications. *Food and Environmental Virology* 2013, 5 (4), 231-235.
33. Akpinar, F.; Yin, J., Characterization of vesicular stomatitis virus populations by tunable resistive pulse sensing. *Journal of Virological Methods* 2015, 218, 71-76.
34. Saleh, O. A.; Sohn, L. L., An Artificial Nanopore for Molecular Sensing. *Nano Letters* 2003, 3 (1), 37-38.
35. Amarasekara, C. A.; Athapattu, U. S.; Rathnayaka, C.; Choi, J.; Park, S.; Soper, S. A., Open-tubular Nanoelectrochromatography (OT-NEC): Gel-free Separation of Single Stranded DNAs (ssDNAs) in Thermoplastic Nanochannels. *Electrophoresis* 2020, 41 (18-19).
36. Harms, 7. D.; Mogensen, K. B.; Nunes, P. S.; Zhou, K.; Hildenbrand, B. W.; Mitra, I.; Tan, Z.; Zlotnick, A.; Kutter, J. P.; Jacobson, S. C., Nanofluidic Devices with Two Pores in Series for Resistive-Pulse Sensing of Single Virus Capsids. *Analytical Chemistry* 2011, 83 (24), 9573-9578.
37. Zhe, J.; Jagtiani, A.; Dutta, P.; Hu, J.; Carletta, J., A micromachined high throughput Coulter counter for bioparticle detection and counting. *Journal of Micromechanics and Microengineering* 2007, 17, 304-313.
38. Becker, H., It's the Economy. *Lab on a Chip* 2009, 9, 2759-2762.
39. Nagura-Ikeda, M.; Imai, K.; Tabata, S.; Miyoshi, K.; Murahara, N.; Mizuno, T.; Horiuchi, M.; Kato, K.; Imoto, Y.; Iwata, M., Clinical evaluation of self-collected saliva by RT-qPCR, direct RT-qPCR, RT-LAMP, and a rapid antigen test to diagnose COVID-19. *Journal of Clinical Microbiology* 2020.
40. Zhao, Z.; Vaidyanathan, S.; Bhanja, P.; Gamage, S.; Saha, S.; Mckinney, C.; Choi, J.; Park, S.; Pahattuge, T.; Wijerathne, H.; Jackson, J. M.; Huppert, M. L.; Witek, M. A.; Soper, S. A., In-plane Extended Nano-coulter Counter (XnCC) for the Label-free Electrical Detection of Biological Particles. *Electroanalysis* 2022, 34, 1-16.
41. Wijerathne, H.; Witek, M. A.; Jackson, J. M.; Brown, V.; Hupert, M. L.; Herrera, K.; Kramer, C.; Davidow, A. E.; Li, Y.; Baird, A. E.; Murphy, M. C.; Soper, S. A., Affinity enrichment of extracellular vesicles from plasma reveals mRNA changes associated with acute ischemic stroke. *Nature Communications Biology* 2021, 3, 613.
42. Pahattuge, T. N.; Jackson, M.; Digamber, R.; Wijerathne, H.; Brown, V.; Witek, M. A.; Perera, C.; Givens, R. S.; Peterson, B. R.; Soper, S. A., Visible photorelease of liquid biopsy markers following microfluidic affinity-enrichment†. *Chemical Communications* 2020, 56, 4098-4101.
43. Manoharan, A.; Choi, J.; Rathnayaka, C.; Vietz, C.; Shiri, F.; Murphy, M. C.; Park, S.; Soper, S. A., Replication of multi-scale Micro/Nano structured on thermoplastics using Nano-injection Molding. *Lab on a Chip* 2022, 22, (submitted for publication).
44. Uba, F. I.; Hu, B.; Weerakoon-Ratnayake, K.; Oliver-Calixte, N.; Soper, S. A., High process yield rates of thermoplastic nanofluidic devices using a hybrid thermal assembly technique. *Lab on a Chip* 2015, 15 (4), 1038-1049.
45. Pan, Y.; Zhang, D.; Yang, P.; Poon, L. L. M.; Wang, Q., Viral load of SARS-CoV-2 in clinical samples. *The Lancet Infectious Diseases* 2020, 20 (4), 411-412.
46. Weatherall, E.; Willmott, G. R., Conductive and Biphasic Pulses in Tunable Resistive Pulse Sensing. *The Journal of Physical Chemistry B* 2015, 119 (16), 5328-5335.
47. Menestrina, J.; Yang, C.; Schiel, M.; Vlassiouk, I.; Siwy, Z. S., Charged Particles Modulate Local Ionic Concentrations and Cause Formation of Positive Peaks in Resistive-Pulse-Based Detection. *The Journal of Physical Chemistry C* 2014, 118 (5), 2391-2398.
48. Wijerathne, H.; Witek, M. A.; Jackson, J. M.; Brown, V.; Hupert, M. L.; Herrera, K.; Kramer, C.; Davidow, A. E.; Li, Y.; Baird, A. E.; Murphy, M. C.; Soper, S. A., Affinity enrichment of extracellular vesicles from plasma reveals mRNA changes associated with acute ischemic stroke. *Communications Biology* 2020, 3 (1), 613.
49. Song. Y.; Song. J.; Wei, X.; Huang. M.; Sun, M.; Zhu, L.; Lin, B.; Shen, H.; Zhu, Z.; Yang, C., Discovery of Aptamers Targeting Receptor-Binding Domain of the SARS-CoV-2 Spike Glycoprotein. 2020.
50. Chai, Z.; Guo, L.; Jin, H.; Li, Y.; Du, S.; Shi, Y.; Wang, C.; Shi, W.; He, J., TBA loop mapping with 3'-inverted-deoxythymidine for fine-tuning of the binding affinity for α-thrombin. *Organic & Biomolecular Chemistry* 2019, 17 (9), 2403-2412.
51. Ni, S. Y., H.; Wang, L.; Lu, J.; Jiang, F.; Lu, A.; Zhang, G., Chemical Modifications of Nucleic Acid Aptamers for Therapeutic Purposes. *Int. J. Mol. Sci.* 2017, 18, 1683.
52. Pahattuge, T. N.; Jackson, J. M.; Digamber, R.; Wijerathne, H.; Brown, V.; Witek, M. A.; Perera, C.; Givens, R. S.; Peterson, B. R.; Soper, S. A., Visible photorelease of liquid biopsy markers following microfluidic affinity-enrichment. *Chemical Communications* 2020, 56 (29), 4098-4101.
53. Gamage, S. S. T.; Pahattuge, T.; Wijerathne, H.; Childers, K.; Vaidyanathan, S.; Athapattu, U. S.; Zhang, L.; Zhao, Z.; Hupert, M. L.; Muller, R. M.; Muller-Cohn, J.; Geisbrecht, B. V.; Pathak, H.; Pessetto, Z.; Gan, G.; Choi, J.; Park, S.; Godwin, A. K.; Witek, M. A.; Soper, S. A., Microfluidic Affinity Selection of Active SARS-CoV-2 Virus Particles *Science Advances* 2022, 8, (accepted for publication).
54. Shu, Y.; McCauley, J., GISAID: Global initiative on sharing all influenza data—from vision to reality. *Euro Surveill* 2017, 22 (13).
55. Scudellari, M., How the coronavirus infects cells—and why Delta is so dangerous. *Nature* 2021, 595 (7869), 640-644.
56. Gamage, S. S. T.; Pahattuge, T. N.; Wijerathne, H.; Childers, K.; Vaidyanathan, S.; Athapattu, U. S.; Zhang, L.; Zhao, Z.; Hupert, M. L.; Muller, R. M.; Muller-Cohn, J.; Dickerson, J.; Dufek, D.; Geisbrecht, B. V.; Pathak, H.; Pessetto, Z.; N. Gan, G.; Choi, J.; Park, S.; Godwin, A. K.; Witek, M. A.; Soper, S. A., Microfluidic Affinity Selection of Active SARS-CoV-2 Virus Particles. *Science Advances* 2022, 8, (accepted for publication).
57. Kim, Y. G.; Yun, S. G.; Kim, M. Y.; Park, K.; Cho, C. H.; Yoon, S. Y.; Nam, M. H.; Lee, C. K.; Cho, Y. J.; Lim, C. S., Comparison between Saliva and Nasopharyngeal Swab Specimens for Detection of Respiratory Viruses by Multiplex Reverse Transcription-PCR. *J Clin Microbiol* 2017, 55 (1), 226-233.

58. R. W. DeBlois and C. P. Bean, *Review of Scientific Instruments,* 1970, 41, 909-916.]

59. E. C. Gregg and K. D. Steidley, *Biophys J,* 1965, 5, 393-405; W. R. Smythe, *The Physics of Fluids,* 1964, 7, 633-638.

The invention claimed is:

1. A nano-Coulter counter device comprising:

an inlet microchannel;

a plurality of nanochannels fluidly coupled to the inlet microchannel having a first cross-dimension, each nanochannel having a nanopore with a second cross-dimension that is narrower than the first cross-dimension, wherein each nanochannel includes an inlet tapered region coupled to an inlet of the nanopore that tapers from the first cross-dimension to the second cross-dimension, wherein each nanopore has the second cross-dimension of at least about 50 nm to about 300 nm, and a pore length of at least about 50 nm to about 300 nm, wherein each nanochannel includes an outlet expansion region coupled to an outlet of the nanopore that expands from the second cross-dimension to a third cross-dimension that is larger than the second cross-dimension;

an outlet microchannel fluidly coupled to an outlet of each of the plurality of nanochannels;

an electrode pair having an electrode at the inlet microchannel and another electrode at the outlet microchannel;

a power source electrically coupled with the electrode pair; and a pump operably coupled with the plurality of nanochannels.

2. The nano-Coulter counter device of claim 1, consisting of five of the nanochannels.

3. The nano-Coulter counter device of claim 1, wherein the inlet tapered region includes an opening at the inlet microchannel.

4. The nano-Coulter counter device of claim 1, wherein the inlet microchannel, plurality of nanochannels, and outlet microchannel are formed of plastic.

5. The nano-coulter counter device of claim 1, wherein the inlet microchannel, plurality of nanochannels, and outlet microchannel are formed of cyclic olefin polymer.

6. A detection system comprising:

a selection device comprising a microfluidic device having a plurality of pillars forming a plurality of flow paths, wherein an affinity-selection agent is coupled to the plurality of pillars by a stimulus-cleavable linker; and the nano-Coulter counter device of claim 1.

7. The detection system of claim 6, wherein the affinity selection agent is selected from a monoclonal antibody or an aptamer.

8. The detection system of claim 6, further comprising a controller configured for controlling operation of the selection device and nano-Coulter counter.

9. The detection system of claim 6, comprising a means for providing stimulus to the stimulus-cleavable linker.

10. The detection system of claim 9, wherein the means for providing the stimulus to the stimulus-cleavable linker is selected from the group consisting of: a chemical input means, wherein the chemical cleaves the linker; light input means, wherein light cleaves the linker; sound input means, where sound cleaves the linker; heat input means, wherein heat cleaves the linker; or combinations thereof.

11. A method of detecting a particle comprising:

providing the nano-Coulter counter of claim 1;

introducing a composition including particles having a particle range of about 50 nm to about 175 nm into the inlet microchannel of the nano-Coulter counter;

applying a voltage with the power source to cause ionic current to flow from one electrode to the other electrode;

recording a current data trace for the current;

detecting a perturbation in the current data trace that is above a threshold; and determining the composition to have the particle.

12. The method of claim 11, wherein:

the flow rate of the composition in the microchannel is from about 0.1 μL/min to 30 μL/min; and the voltage of the power source is from about 1 V to about 5 V.

13. The method of claim 11, wherein the nano-Coulter counter has a limit of detection of at least about $2.4\times10^3$ particles/mL, or within 25% thereof.

14. A method of detecting a particle comprising:

providing the detection system of claim 6;

introducing a sample suspected of having particles into the selection device;

capturing the particles with the affinity-selection agent;

releasing the particles from the pillars into a composition by cleavage of the stimulus-cleavable linker;

introducing the composition including particles having a particle size range of about 50 nm to about 175 nm into the inlet microchannel of the nano-Coulter counter;

applying a power source to cause current to flow from one electrode to the other electrode;

recording a current data trace for the current;

detecting a perturbation in the current data trace that is above a threshold; and determining the composition to have the particle.

15. The method of claim 14, comprising controlling fluid flow in the nanochannels with the pump.

* * * * *